(12) United States Patent
Steele et al.

(10) Patent No.: US 9,801,831 B2
(45) Date of Patent: Oct. 31, 2017

(54) DEVICE FOR CONTROLLED RELEASE OF A BIOACTIVE AGENT

(75) Inventors: Terry W. J. Steele, Singapore (SG); Say Chye Joachim Loo, Singapore (SG); Subramanian Venkatraman, Singapore (SG); Yin Chiang Freddy Boey, Singapore (SG)

(73) Assignee: Nanyang Technological University, Singapore (SG)

( * ) Notice: Subject to any disclaimer, the term of this patent is extended or adjusted under 35 U.S.C. 154(b) by 675 days.

(21) Appl. No.: 13/977,332

(22) PCT Filed: Dec. 29, 2011

(86) PCT No.: PCT/SG2011/000457
§ 371 (c)(1),
(2), (4) Date: Jun. 28, 2013

(87) PCT Pub. No.: WO2012/091680
PCT Pub. Date: Jul. 5, 2012

(65) Prior Publication Data
US 2013/0281977 A1   Oct. 24, 2013

Related U.S. Application Data

(60) Provisional application No. 61/428,514, filed on Dec. 30, 2010, provisional application No. 61/428,531, filed on Dec. 30, 2010.

(51) Int. Cl.
*A61K 9/51*   (2006.01)
*A61K 9/70*   (2006.01)
*A61M 25/10*   (2013.01)

(52) U.S. Cl.
CPC .......... *A61K 9/7007* (2013.01); *A61K 9/5153* (2013.01); *A61F 2250/0067* (2013.01); *A61M 2025/105* (2013.01)

(58) Field of Classification Search
CPC .................................................... A61K 9/5153
See application file for complete search history.

(56) References Cited

U.S. PATENT DOCUMENTS 5,102,402 A * 4/1992 Dror ................. A61F 2/958
604/103.02
5,413,924 A * 5/1995 Kosak ................ C12Q 1/68
435/177

(Continued)

FOREIGN PATENT DOCUMENTS

EP         1 808 167      12/2006
WO    WO 2003/030941      4/2003

(Continued)

OTHER PUBLICATIONS

S. Venkatratraman, et al., "Release profiles in drug-eluting stents, issues and uncertainties," 2007 Journal of Controlled Release, vol. 120, pp. 149-160.

(Continued)

*Primary Examiner* — Benjamin Packard
(74) *Attorney, Agent, or Firm* — Schiff Hardin LLP

(57) ABSTRACT

Present invention relates to a device for controlled release of a bioactive agent. The device comprises a thin film located on the surface of the device, wherein said thin film comprises a bioactive agent-containing layer comprising a polymeric matrix and at least one bioactive agent.

19 Claims, 16 Drawing Sheets

(56) References Cited

U.S. PATENT DOCUMENTS

| | | | |
|---|---|---|---|
| 7,030,127 | B2 | 4/2006 | Nathan et al. |
| 7,034,037 | B2 | 4/2006 | Arnold et al. |
| 7,220,433 | B2 * | 5/2007 | Cui .................. A61K 9/5073 424/400 |

FOREIGN PATENT DOCUMENTS

| | | | |
|---|---|---|---|
| WO | WO 2007/146049 | 12/2007 | |
| WO | WO 2008/002657 | 1/2008 | |
| WO | WO 2009/036083 | 3/2009 | |
| WO | WO 2009/046446 | 4/2009 | |
| WO | WO 2010/009335 | 1/2010 | |
| WO | WO 2010009335 A1 * | 1/2010 | ........... A61L 17/005 |
| WO | WO 2010/093333 | 8/2010 | |

OTHER PUBLICATIONS

P. Stella. "Drug eluting Balloon in Bifurcations Trial (DEBIUT)", Periodical, 2010, http://clinicaltrials.gov.
I. Mukherjee, INDICOR The Pacilitaxel-Eluting PTCA-Balloon in Catheter in Combination with a Cobalt-Chromium Stent, Periodical (Online), 2010, http://clinicaltrials.gov.
B. Scheller, et al., "Pacitaxel Balloon Coating, a Novel Method for Prevention and Therapy of Restenosis", 2004, Circulation, vol. 110, pp. 810-814.
B. Scheller, et al., "Two year follow-up after treatment of coronary in-stent restenosis with a paclitaxel-coated balloon catheter", 2008, Clinical Research in Cardiology, Vo. 97, pp. 773-781.
B. Scheller, et al., "Treatment of Coronary In-Stent Restenosis with Paclitaxel-Coated Balloon Catheter", 2006, The New England Journal of Medicine, vol. 365, pp. 2113-21124.
C. Herdeg, et al, "Local Pacitaxel Delivery for the Prevention of Restenosis Biological Effects and Efficacy In Vivo", 2000, Journal of the American College of Cardiology, vol. 35 pp. 1969-1976.
D. Axel, et al., "Paclitaxel Inhibits Arterial Smooth Muscle Cell Proliferation and Migration in Vitro and In Vivo Local Drug Delivery", 1997, Circulation, vol. 96, p. 636-645.
F. Burzotta, Intimal Hyperplasie Evaluated by Optical Coherence Tomography (OCT) in de Novo Coronary Lesions Treated by Drug-eluting Balloon and Bare-metal Stent (IN-PACT CORO) 2010, http://clinicaltrials.gov.
B. Scheller, Efficacy of the Sequent® Please in the Treatment of denovo Stenoses Versus Taxus™ 2010, Liberte™ (PEPCAD-DEBonly) http://clinicaltrials.gov.
A.Simmons, et al, "Bistability and biological performance of a PDMS-based polyurethane for controlled drug release" 2008, Biomaterials, pp. 2987-2995.
R.K. Malcolm, et al., "Controlled release of a model antibacterial drug from a novel self-lubricating silicone biomaterial", 2004, Journal of Controlled Release, vol. 97, pp. 313-320.
A.de Queiroz, et al., Controlled release of 5-fluorouridine from radiation-crosslinked poly(ethylene-co-vinyl acetate) films, 2006, Acta Biomaterials, pp. 641-650.
J.Siepmanan, et al., "Mathematical modeling of drug delivery" 2008, International Journal of Pharmaceutics, vol. 364, pp. 328-343.
RK. Malcolm, et al, "Long-term controlled release of the HIV MICROBIDE TMC120 from silicone elastomer vaginal rings", 2005 Journal of Antimicrobial Chemotherapy, vol. 56, pp. 954-956.
R. Arnold, et al. Antimicrobial Activity and Local Release Characteristics of Chlorhexidine Diacetate Loaded within the Denial Copolymer Matrix Ethylene Vinyl Acetate, 2008. vol. 86 Journal of Biomedical Matter Research, pp. 506-513.
N.Chia, et al., "Controlled degradation of multilayered poly(lactide-co-glycolide) films using electron beam irradiation" 2008, Journal of Biomedical Materials Research, vol. 84 A, pp. 980-987.
X.T.Wang, et al., Effects of controlled-released sirolimus from polymer matrices on human coronary artery smooth muscle cells 2007, Journal of Biomaterials Science Polymer Edn, vol. 18 pp. 1401-1414.
H.Kranz, et al. "A novel in situ forming drug delivery system for controlled parenteral drug delivery" 2007, Internatoinal Journal of Pharmaceutics, vol. 332, pp. 107-114.
B.S. Kim, et al. "Insulin-Loaded Microcapsules for In Vivo Delivery", 2009, vol. 6, pp. 353-365.
SCJ. Loo., et al., "Drug Release Form Irradiated PLGA and PLLA Multi-layered Films" 2010, vol. 58, pp. 3060-3071.
M.L. Forrest, et al., "In vitro release of the m TOR inhibitor rapamycin from poly(ethylene glycol)-b-poly($\epsilon$-caprolactone) micelles" 2006, Journal of Controlled Release vol. 110, pp. 370-377.
M.L.Forrest. et al. "Paclitaxel Prodrugs with Sustained Release and High Solubility in poly(ethylene glycol)-b-poly($\epsilon$-caprolactone) Micelle Nanocarriers: Pharmacokinetic Dispoistion, Tolerability, and Cytotoxicity" 2008 Pharmaceutical Research, vol. 25, pp. 194-206.
J.Liu, "Lipsome formulation of a novel hydrophobic aryl-imidazole compound for anit-cancer therapy" 2006, Cancer Chemotherapy Pharmacology vol. 58, pp. 306-318.
A.Belu, et al., "Chemical imaging of drug eluting coatings: Combing surface analysis and confocal Raman microscopy" 2008, Journal of Controlled Release vol. 126, pp. 111-121.
D.Narayan, et al., "Effect of pore size and interpore distance on endothelial cell growth on polymers" 2008, Journal of Biomedical Materials Resesarch, vol. 87, pp. 710-717.
W.L.Murphy, et al., "Sustained release of vascular endothelial growth factor form mineralized poly(lactide-co-glycolide), scaffolds for tissue engineering" 2000, Biomaterials, pp. 2521-2527.
B.Ong, et al., Paclitaxel delivery from PLGA foams for controlled release in post-surgical chemotherapy against glioblastioma multifome 2009, Biomaterials, pp. 3189-3196.
F.Wang, et al., "PEG modulated release of etanidazole from implantable PLGA/PDLA disc" 2002, Biomaterials, vol. 23, pp. 3555-3566.
X.Wang, et al., Controlled release of siriollmus from multilayered PLGA stent matrix, 2007, Biomaterials, vol. 27, pp. 5588-5595.
E.Kang, et al., "Paclitaxel distribution in poly(ethylene glycol)/poly(lactide-co-glycolic acid) blends and its release visualized by coherent anti-Stokes Raman scattering microscopy" 2007, Journal of Controlled Release, vol. 122, pp. 261-268.
L.P. Tan, et al., "Effect of plasticization on heparin release from biodegradable matrices" 2004, pp. 89-96.
A. Santovena, et al., "Structural properties of biodegradable polyesters and rheological behaviour of their dispersions and films" 2005, Journal of Biomaterials Science Polymer Edition, vol. 16, pp. 629-641.
E.Widjaja, et al. "Band-Target Entropy Minimization, A Robust Algorithm for Pure Component Spectral Recovery, Application to Complex Randomized Mixtures of Six Components" 2003, Analytical Chemistry, vol. 75, pp. 4499-4507.
E.Widjaja, et al. "Application of Raman microscopy and band-target entropy microscopy and band-target entropy minimization to identify minor components in model pharmaceutical tablets", 2008, Journal of Pharmaceutical and Biomedical Analysis pp. 274-281.
E.Widjaja, et al, "Use of Raman Microscopy and Band-Target Entropy Minimization Analysis to Identify Dyes in a Commerical Stamp. Implications for Authentication and Counterfeit Detection" 2008, vol. 80, pp. 729-733.
A. Zhu, et al., "Adhesion contact dynamics of 3T3 fibroblast on poly(lactide-co-glycolide acid) surface modified by photochemical immobilization of biomacromolecules" 2006, Biomaterials, vol. 27, 2566-2576.
Y.Wan., et al., "Characterization of Surface property of poly(lactide-co-glycolide) after oxygen plasma treatment" 2004, pp. 4777-4783.
J.K.Maxfield, et al., "Conformation of poly(ethylene oxide)in the solid state, melt and solution measeured by Raman scattering", 1976, vol. 16, pp. 505-509.
J.Jackson, et al., Characterization of perivascular poly(lactic-co-glycolic acid) films containing paclitaxel, 2004, vol. 97-109.
T.Ooya, et al., "Effects of ethylene glycol-based graft, star-shaped and dendritic polymers on solubilzation and controlled released of paclitaxel" 2003, Journal of Controlled Release vol. 93, pp. 121-127.

(56) References Cited

OTHER PUBLICATIONS

C.H Liu, et al., "Permeation of Protein From Porous Poly(ε-caprolactone) films", 2003, Journal of Biomedical Materials Research, vol. 89, pp. 179-225.
W.J.Lin, et al., "Design of a microporous controlled delivery system for theophylline tablets", 2003, Journal of Controlled Release, vol. 89, pp. 179-187.
U.Westedt, et al., "Paclitaxel releasing films consisting of poly(vinyl alcohol)-graft-poly(lactide-co-glycolide) and their potential as biodegradable stent coatings" 2006, Journal of Controlled Release, vol. 111, pp. 235-246.
S.Park, et al. "Surface Modification of Poly(ethylene terephthalate) Angioplasty Balloons with a Hydrophilic Poly(acrylamide-co-ethlene glycol)Interpenetrating Polymer Network Coating", 2000, Journal of Biomedical Materials Research (Appl Biomaterials), vol. 53, pp. 568-576.

\* cited by examiner

DEVICE FOR CONTROLLED RELEASE OF A BIOACTIVE AGENT

CROSS-REFERENCE TO RELATED APPLICATION

This application claims the benefit of priority of U.S. Provisional Patent Application No. 61/428,514, filed 30 Dec. 2010, and U.S. Provisional Patent Application No. 61/428,531, filed 30 Dec. 2010, the contents of which being hereby incorporated by reference in their entireties for all purposes.

TECHNICAL FIELD

The invention relates to a device for controlled release of a bioactive agent, comprising a bioactive agent-containing thin film, including devices that are introduced into a subject via a surgical procedure.

BACKGROUND

Atherosclerotic blood vessels treated with percutaneous transluminal coronary angioplasty (PTCA) balloons (with or without stents) have been shown to have a better clinical outcome if they can be immediately treated with anti-restenosis drugs. This has led to designs of stent coatings incorporating slow release of paclitaxel and other anti-restenosis agents. Stent implementation or administration, however, carries a long term risk of spontaneous thrombosis, thereby requiring daily use of anti-platelet drugs.

Methods to deliver anti-restenosis agents (e.g. paclitaxel and rapamycin) without stents typically take the form of modified PTCA angioplasty balloon catheters such as double balloon catheters and porous balloons. These devices tend to be cumbersome and can cause additional vascular injury. More recently, drug-eluting balloons have been developed using conventional balloon catheters, usually via surface modification.

Preliminary findings have also demonstrated positive proof-of-concept data. Using a simple solvent coating procedure, Scheller et al. (*Circulation*. 2004 Aug. 17; 110(7): 810-4. Epub 2004 Aug. 9) coated PTCA angioplasty balloon catheters with paclitaxel and proceeded to test them against bare metal stents in porcine coronary arteries. The coating was found to be safe and as effective in restenosis inhibition as drug eluting stents. However, efficacy of the drug eluting stents and the paclitaxel-coated balloon catheters were not directly compared. A clinical trial involving 52 patients was subsequently done comparing paclitaxel-coated balloon to uncoated balloons (Scheller et al., *N Engl J Med*. 2006 Nov. 16; 355(20):2113-24. Epub 2006 Nov. 13). After 12 months, major adverse cardiac events was 31% in the untreated controls and 4% in the paclitaxel-coated balloon group. A two-year follow-up with a total of 108 patients demonstrated continued restenosis inhibition (Scheller et al., *Clin Res Cardiol*. 2008 October; 97(10):773-81. Epub 2008 Jun. 5).

Currently, the drug-eluting balloons focus predominantly on 2 designs: drugs incorporated onto a porous surface and drugs incorporated into a "transfer" agent, such as iopromide (as a contrast agent). The DIOR® drug-eluting balloon is an example of the pore-incorporated paclitaxel, while the PAC-COCATH® technology developed by Braun is an example of the latter design. Other transfer agents such as urea and shellac are also popular.

Nevertheless, there are some inherent limitations in the current designs. The paclitaxel-coated balloons inherently involve erratic (non-predictable) drug delivery. This is particularly troublesome because the bolus amount varies with the skill of the practitioner and thus the delivered dose is highly variable, which is undesirable. Further, there is no sustained drug delivery beyond the initial 2 to 3 days after administration of the balloons.

Therefore, there remains a need to provide for an improved bioactive-eluting device to overcome, or at least alleviates, the above problems.

SUMMARY

According to one aspect of the invention, there is provided a device for controlled release of a bioactive agent. The device comprises a thin film located on the surface of the device, wherein said thin film comprises a bioactive agent-containing layer comprising a polymeric matrix and at least one bioactive agent.

According to another aspect of the invention, there is provided a method of delivering a bioactive agent to a target site of a subject, comprising contacting the device according to the present invention with said subject.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and variations may be made without departing from the scope of the invention. The various embodiments are not necessarily mutually exclusive, as some embodiments can be combined with one or more other embodiments to form new embodiments.

The present invention provides an improved device that allows localised drug delivery at a target site of a subject and at the same time achieves controlled/sustained release of the drug (or bioactive agent) at the target site. A sustained release of about 10 to 60 days has been demonstrated. Controlled burst release up to 50% of the loaded drug has been achieved.

Figure 9:
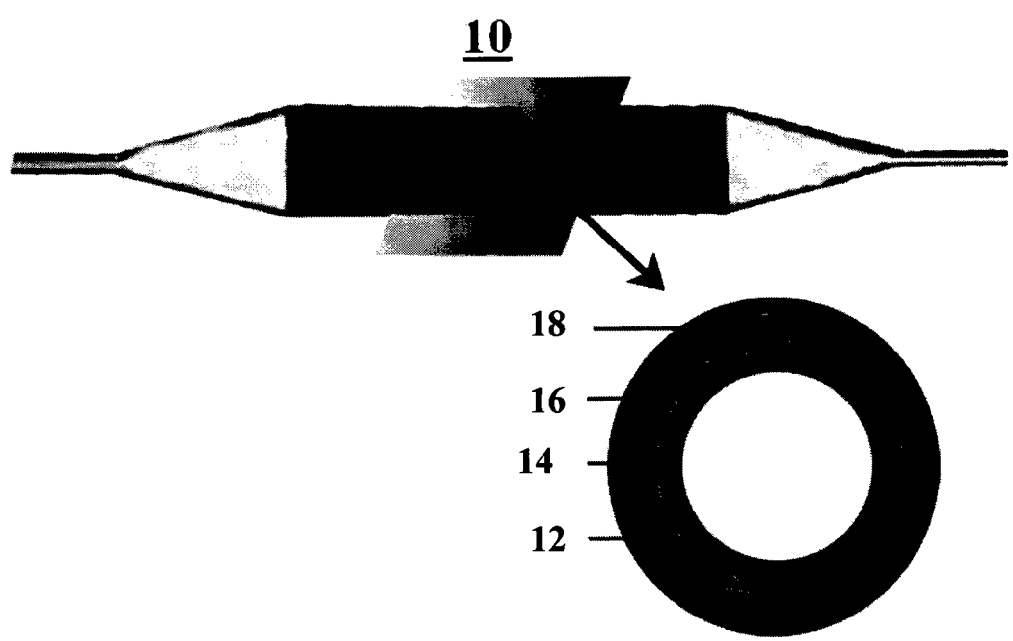
FIG. 9 shows an illustrative diagram of the present device.

In one aspect of the invention illustrated in FIG. 9, there is provided a device 10 for controlled release of a bioactive agent. The device 10 includes a thin film 16 located on the surface 12 of the device, wherein said thin film includes a bioactive agent-containing layer including a polymeric matrix and at least one bioactive agent.

In various embodiments, the device may be an implant, a surgical instrument or a catheter.

In one embodiment, the device may be an angioplasty balloon catheter for releasing anti-restenotic agents (ARAs) such as paclitaxel (PCTX). For the ease of discussion and understanding of the present invention, the following paragraphs describe the invention in relation to an angioplasty balloon catheter but it is to be understood and appreciated that the scope of the invention is not limited to such in any way.

The present device includes a thin film located on the surface of the device. In the present context, a "thin film" generally refers to a continuous layer having a mean thickness of between 10 nm and 500 µm. The thin film may also be comprised of more than one layer. For example, the thin film may comprise of a bioactive agent-containing layer and an adhesive layer, and optionally a release layer (see discussion below). Films having a mean thickness of less than 10 nm may be difficult to manufacture and may not possess sufficient mechanical strength. Further, discrete regions of the material or a discontinuous layer may result instead. Due to its intended purpose of use as an implant, structural configuration of the device may restrict the thickness of the thin film to about 500 µm.

In various embodiments, the thin film is carefully designed and engineered to be bioadhesive, bio-absorbable and biodegradable, that is capable of sustaining delivery of a bioactive agent for a prolonged period of time, for example hours, days, weeks or months. The thin film can be delivered by a typical angioplasty balloon (or other modified balloon/catheter) and will subsequently transfer to the arterial wall upon balloon inflation. This allows local drug delivery, i.e. very small doses to the tissues that need it most. This mode of delivery decreases the likelihood of systemic toxicity which is commonly associated with drugs. By engineering the angioplasty balloon and drug encapsulated film in this manner, a wide range of therapeutic agents, drug pharmacokinetics, and local delivery sites can be achieved. This yields a new type of medical device that can target a plethora of vascular diseases including stroke, kidney failure, peripheral artery diseases, and coronary atherosclerosis. For example, as an alternative to conventional ureteral stent, the device of the invention may be implanted in the urinary tract to deliver antibiotics to the infected site such as the ureter.

Typically, the angioplasty balloon catheter has a hollow cylindrical shape. The thin film is located on the external surface of the balloon where when the balloon is inflated in the radially outward direction, the thin film contacts the tissue and adheres to the tissue.

The thin film includes a bioactive agent-containing layer including a polymeric matrix and at least one bioactive agent.

The bioactive agent to be delivered by the device of the present invention may be pharmaceutical, therapeutic, immunological agents, sensitizing agents, diagnostic or prophylactic agents. The agent may be, for example, a small molecule, nucleic acid, protein, peptide, drug, vaccine, virus, etc. The agent may be described as a single compound or a combination of compounds.

In one embodiment, the bioactive agent is a compound with pharmaceutical activity, such as a clinically useful drug. Suitable drugs include, but are not limited to, antibiotics, anti-viral agents, anesthetics, steroidal agents, anti-inflammatory agents including non-steroidal anti-inflammatory agents, anti-neoplastic agents, antibodies, decongestants, antihypertensives, sedatives, contraceptives, progestational agent, anti-cholinergic agents, analgesics, anti-depressants, anti-psychotics, diuretic agents, cardiovascular active agents, and vasoactive agents. For example, the drug may be paclitaxel or rapamycin.

In another embodiment, the bioactive agent to be delivered may also be an agent for use in diagnosis or screening. Diagnostic agents that can be delivered in vivo include gases, metals, commercially available imaging agents used in positron emission tomography (PET), computer assisted tomography (CAT), x-ray, fluoroscopy, and magnetic resonance imaging (MRI), as well as contrast agents. Examples of suitable materials for use as contrast agents in MRI include gadolinium chelates, as well as iron, magnesium, manganese, copper, and chromium or their chelates. Examples of materials useful for CAT and x-ray imaging include iodine-based materials.

Prophylactic agents that can be delivered include, but are not limited to, antibiotics, nutritional supplements, and antigens or vaccines. Antigens or vaccines may comprise isolated proteins or peptides, inactivated organisms and viruses, dead organisms and viruses, genetically altered organisms or viruses, and cell extracts. The prophylactic agents may also include nucleoside type drugs, which nucleoside may for example be plasmid DNA, antisense DNA, double stranded DNA, single stranded DNA, RNA, microRNA, siRNA.

"Polymeric matrix" as used in the present context has the common understanding known in polymer science. It generally refers to a network of polymers whose chains interact and entangle with one another and such interactions tend to fix the individual chains more strongly in position and resist deformations and matrix breakup, thereby affording structural strength and integrity to the polymerix matrix.

The polymeric matrix may include a biocompatible polymer. The term "biocompatible polymer" (which also can be referred to as "tissue compatible polymer"), as used herein, is a polymer that produces little, if any, adverse biological response when used in vivo. The term thus generally refers to the inability of a polymer to promote a measurably adverse biological response in a cell, including in the body of an animal, including a human. A biocompatible polymer can have one or more of the following properties: non-toxic, non-mutagenic, non-allergenic, non-carcinogenic, and/or non-irritating. A biocompatible polymer, in the least, can be innocuous and tolerated by the respective cell and/or body. A biocompatible polymer, by itself, may also improve one or more functions in the body. A variety of biocompatible polymers is suitable for the polymeric matrix. The biocompatible polymers can be synthetic polymers, naturally occurring polymers or combinations thereof. As used herein the term "synthetic polymer" refers to polymers that are not found in nature, including polymers that are made from naturally occurring biomaterials. Examples of suitable biocompatible polymers include non-absorbable polymers such as polypropylene, polyethylene, polyethylene terephthalate, polytetrafluoroethylene, polyaryletherketone, nylon, fluorinated ethylene propylene, polybutester, and silicone, or copolymers thereof (e.g., a copolymer of polypropylene and polyethylene); absorbable polymers such as polyglycolic acid (PGA), polylactic acid (PLA), polycaprolactone, and polyhydroxyalkanoate, copolymers thereof (e.g., a copolymer of PGA and PLA), and mixtures thereof.

A wide variety of biodegradable polymers is also suitable for the polymeric matrix. Biodegradable polymers, as defined herein, are polymers that gradually disintegrate or are absorbed in vivo over a period of time (e.g., within months or years). Biodegradable polymers may be a subset of biocompatible polymers. Disintegration may for instance occur via hydrolysis, may be catalysed by an enzyme and may be assisted by conditions to which the microparticles are exposed in the cell. Examples of biodegradable polymers include, but are not limited to, polyesters, polyanhydrides, polyorthoesters, polyphosphazenes, polyphosphates, polyphosphoesters, polyphosphonates, polydioxanones, polyhydroxyalkanoates, polycarbonates, polyalkylcarbonates, polyorthocarbonates, polyesteramides, polyamides, polyamines, polypeptides, polyurethanes, polyetheresters, or combinations thereof. An illustrative example of a biodegradable polymer is poly (α-hydroxy acid), for example polylactic acid, polyglycolic acid and copolymers and mixtures thereof such as poly(L-lactide) (PLLA), poly(D,L-lactide) (PLA), poly(glycolide) (PGA), poly(L-lactide-co-D,L-lactide) (PLLA/PLA), poly(lactide-co-glycolide) (PLGA), poly(glycolide-co-trimethylene carbonate) (PGA/PTMC), poly(D,L-lactide-co-caprolactone) (PLA/PCL), poly(glycolide-co-caprolactone) (PGA/PCL), polyethylene oxide (PEO), polydioxanone (PDS), polypropylene fumarate, poly(ethyl glutamate-co-glutamic acid), poly(tert-butyloxy-carbonylmethyl glutamate), poly(carbonate-esters), polyethylene glycol (PEG), PEG fatty acid esters, polyvinyl pyrrolidone (PVP), polyvinyl alcohol (PVA), hydroxy propyl cellulose. Further examples of suitable biodegradable polymers include a polylacton such as a poly(ε-caprolactone) (PCL) and copolymers thereof such as polycaprolactone co-butylacrylate; polyhydroxybutyrate (PHBT) and copolymers of polyhydroxybutyrate; poly(phosphazene); poly(phosphate ester); a polypeptide; a polydepsipeptide, a maleic anhydride copolymer; a poly-phosphazene; a polyiminocarbonate; poly(dimethyl-trimethylene carbonate-co-trimethylene carbonate); a polydioxanone, polyvalerolactone, a polyorthoester, a polyanhydride, polycyanoacrylate; a tyrosine-derived polycarbonate or polyester-amide; a polysaccharide such as hyaluronic acid; and copolymers and mixtures of the above polymers, among others. In some embodiments the biocompatible polymer may be cross-linked, for example to improve mechanical stability of the matrix.

In certain embodiments, the polymeric matrix is formed from a biocompatible polymer, such as a biodegradable polymer. It may for instance be formed from a poly(α-hydroxy acid), such as a poly(lactide) ("PLA"), a copolymer of lactide and glycolide, such as a poly(D,L-lactide-co-glycolide) ("PLGA"), or a copolymer of D,L-lactide and caprolactone. PLGA polymers include those having a lactide/glycolide molar ratio such as 20:80, 25:75, 40:60, 45:55, 53:47, 55:45, 60:40, 75:25, and 80:20, and having a molecular weight ranging, for example, from 5,000 to 10,000 to 20,000 to 40,000 to 50,000 to 70,000 to 100,000 to 200,00 Daltons. Yet further illustrative examples of a biocompatible polymer are collagen, chitosan, alginate, heparin, gelatin and hyaluronic acid, all naturally occurring polymers. Polyhydroxybutyrate (supra) is a polyester produced as granules by microorganisms.

In various embodiments, the polymeric matrix of the bioactive agent-containing layer includes a polymer selected from the group consisting of polyethylene glycol (PEG), PEG fatty acid esters, poly-L-lactic acid (PLLA), poly (lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, and combinations thereof.

In one embodiment, the polymeric matrix includes PLGA and/or PEG. The polymeric matrix may include between 0 and 50% by weight PEG with the balance being PLGA, for example, 0 wt %, 5 wt %, 10 wt %, 15 wt %, 20 wt %, 25 wt %, 30 wt %, 35 wt %, 40 wt %, 45 wt %, or 50 wt % PEG. The PEG may have a molecular weight of between 0.4 kDa and 500 kDa, such as 0.4 kDa, 0.8 kDa, 1 kDa, 4 kDa, 8 kDa, 10 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 150 kDa, 200 kDa, 250 kDa, 300 kDa, 350 kDa, 400 kDa, 450 kDa, or 500 kDa.

In alternative embodiments, the polymeric matrix includes PEG fatty acid esters. For example, the PEG fatty acid ester may be PEG distearate. The polymerix matrix may further include one or more fatty acids or fatty alcohols such as cetyl alcohol. In one embodiment, the polymeric matrix includes 50 to 99% by weight 400 Da PEG distearate and 1 to 50% cetyl alcohol.

Particles, including microparticles and nanoparticles, may be supported or located in the polymeric matrix.

As used herein, the term "microparticle" refers to a microscopic particle with a size measured in micrometres (μm). Typically, the microparticle has an average width, including diameter, of from about 1 µm to about 500 µm, such as an average diameter of from about 1 µm to about 50 µm, for instance from about 1 µm to about 25 µm. In some embodiments the microparticle has a diameter of maximally about 5 microns. In some embodiments the microparticle has a diameter of at least about 2 microns. In particular, the microparticle may have an average diameter of from about 1 µm to about 10 µm, such as about 1 µm to about 7 µm, about 1 µm to about 6 µm, about 1 µm to about 5 µm, about 1.5 µm to about 5 µm, about 2 µm to about 5 µm, about 2 µm to about 6 µm, about 2.5 µm to about 5 µm, about 2.5 µm to about 6 µm, about 3 µm to about 6 µm, about 3 µm to about 5 µm, about 4 µm to about 6 µm or about 4 µm to about 5 µm.

As used herein, the term "nanoparticle" refers to a nanoscopic particle with a size measured in nanometres (nm). Typically, the nanoparticle has an average width, including diameter, of from about 1 nm to about 500 nm, such as an average diameter of from about 1 nm to about 50 nm, for instance from about 1 nm to about 25 nm. In some embodiments the nanoparticle has a diameter of maximally about 5 nm. In some embodiments the nanoparticle has a diameter of at least about 2 nm. In particular, the nanoparticle may have an average diameter of from about 1 nm to about 10 nm, such as about 1 nm to about 7 nm, about 1 nm to about 6 nm, about 1 nm to about 5 nm, about 1.5 nm to about 5 nm, about 2 nm to about 5 nm, about 2 nm to about 6 nm, about 2.5 nm to about 5 nm, about 2.5 nm to about 6 nm, about 3 nm to about 6 nm, about 3 nm to about 5 nm, about 4 nm to about 6 nm or about 4 nm to about 5 nm.

In various embodiments, the bioactive agents may be encapsulated in such microparticles or nanoparticles which are supported or loaded into the bioactive agent-containing layer. In yet another embodiment, the bioactive agents may be encapsulated in a mixture of microparticles and nanoparticles (and collectively may be called particles). Each of the particles may have a mean diameter of between 1 nm and 500 µm. The particles may have a core-shell structure and the bioactive agents may be encapsulated in the core of the particle. In various embodiments, the particles are essentially monodisperse. In other embodiments, the particles may be polydisperse.

In various embodiments, the bioactive agent-containing layer includes 1-50% by weight of the bioactive-encapsulating particles. For example, the bioactive agent-containing layer may include 1 wt %, 5 wt %, 10 wt %, 15 wt %, 20 wt %, 25 wt %, 30 wt %, 35 wt %, 40 wt %, 45 wt %, or 50 wt % of the bioactive-encapsulating particles.

In various embodiments, the particle may include or consist of a biodegradable material. Suitable biodegradable materials for the particles include those previously discussed with respect to the polymeric matrix. Additionally, the biodegradable material may be selected from the group consisting of polyesters, poly-anhydrides, poly-amides, poly-ketals, poly-acetals, poly-acrylates, lipids, chitosan and gelatin. For example, the polyesters may be selected from PEG, PLLA, PGLA, PVA, PVP, PCL and combinations thereof.

In alternative embodiments, the bioactive agents may form the microparticles or nanoparticles. The bioactive agent particles may be supported or loaded in the polymeric matrix of the bioactive agent-containing layer directly without further encapsulation.

In various embodiments, the thin film 16 may further include an adhesive layer 18 on top of the bioactive agent-containing layer, wherein the bioactive agent-containing layer lies between the adhesive layer and the device surface as illustrated in FIG. 9.

As mentioned above, upon introduction of the angioplasty balloon catheter to the target site, the thin film may adhere to the neighbouring tissue when inflated, thereby allowing delivery of the bioactive agent to the tissue. The inclusion of an adhesion layer in the thin film helps to improve the adhesion of the thin film to the tissue, thereby improving the efficacy of the drug delivery.

In one embodiment, the adhesive layer is a bioadhesive layer. The bioadhesive layer is usually not incorporated with a bioactive agent (i.e. bioactive agent-free or incorporated with minute amount of bioactive agent). However, in certain embodiments it can also comprise a bioactive agent that may be the same or a different one than that in the bioactive agent-containing underlying layer. In such embodiments, the bioactive agent can be in nanoparticulate form or microparticluate form, and is well-dispersed or dissolved within the bioadhesive layer. Thus, in various embodiments bioactive agent is incorporated into each of the bioactive agent-containing layer and the bioadhesive layer.

The bioadhesive may be selectable from polyacrylic acid (PAA) type adhesives sold under trade names such as Carbopol or Polycarbophil. These PAAs may be crosslinked further to yield better adhesion. The bioactive agent particles or particles encapsulating the bioactive agents may be reduced to nanometer size and then dispersed/dissolved in the bioadhesive layer by using suspension methods. In other words, the bioactive agent is dissolved or suspended in a solution of the bioadhesive, and then coated or cast on to the catheter balloon directly. In this manner, there is a maximum possible loading of the bioactive agent. Other suitable bioadhesive materials include chitosan of sufficient degree of de-acetylation (>~70%), gelatin or collagen denatured sufficiently to dissolve in aqueous media, polyvinyl alcohol having a degree of hydrolysis ranging from 85% to 99% with or without boric acid added to crosslink it, hydroxylpropyl cellulose, or polyvinyl pyrrolidone crosslinked sufficiently to yield an adhesive.

Another advantage of adding the bioadhesive layer becomes apparent when the effective bioactive agent amount required for sustained delivery is too high to be loaded into a single layer. In this case, the bioadhesive layer may be incorporated with a bioactive agent while the underlying bioactive agent-containing layer contains most of the bioactive agent. As mentioned earlier, different types of bioactive agent may also be incorporated into each of the respective layer.

In various embodiments, the adhesive layer is biodegradable, as defined previously.

In various embodiments, the thin film may further include a release layer 14 between the bioactive agent-containing layer and the device surface.

After the thin film (or the adhesive layer, if present) adheres to the tissue, the balloon is deflated. It is essential that the adhesion force between the thin film (or the adhesive layer) and the tissue is larger than the adhesion force between the thin film and the balloon surface. Otherwise, the thin film (or the adhesive layer) will delaminate from the tissue when the balloon deflates. To reduce the likelihood of the thin film (or adhesive layer) delaminating from the tissue when the balloon deflates, the release layer is positioned between the bioactive agent-containing layer in the thin film and the device surface. The release layer serves to delaminate the thin film from the balloon surface so that the thin film stays adhered to the tissue when the balloon is deflated.

In various embodiments, the release layer is composed of a polyester wax. The release layer may have a melting temperature of between 35 and 40° C. For example, the polyester wax may include a PEG fatty acid ester. The polyester wax may further include one or more fatty acids or fatty alcohols. The low melting temperature allows the thin film to be readily released from the underlying device surface if introduced into the body of a subject and may be selected in view of the body temperature of the subject.

In various embodiments, the release layer is biodegradable, as defined previously.

Figure 10:
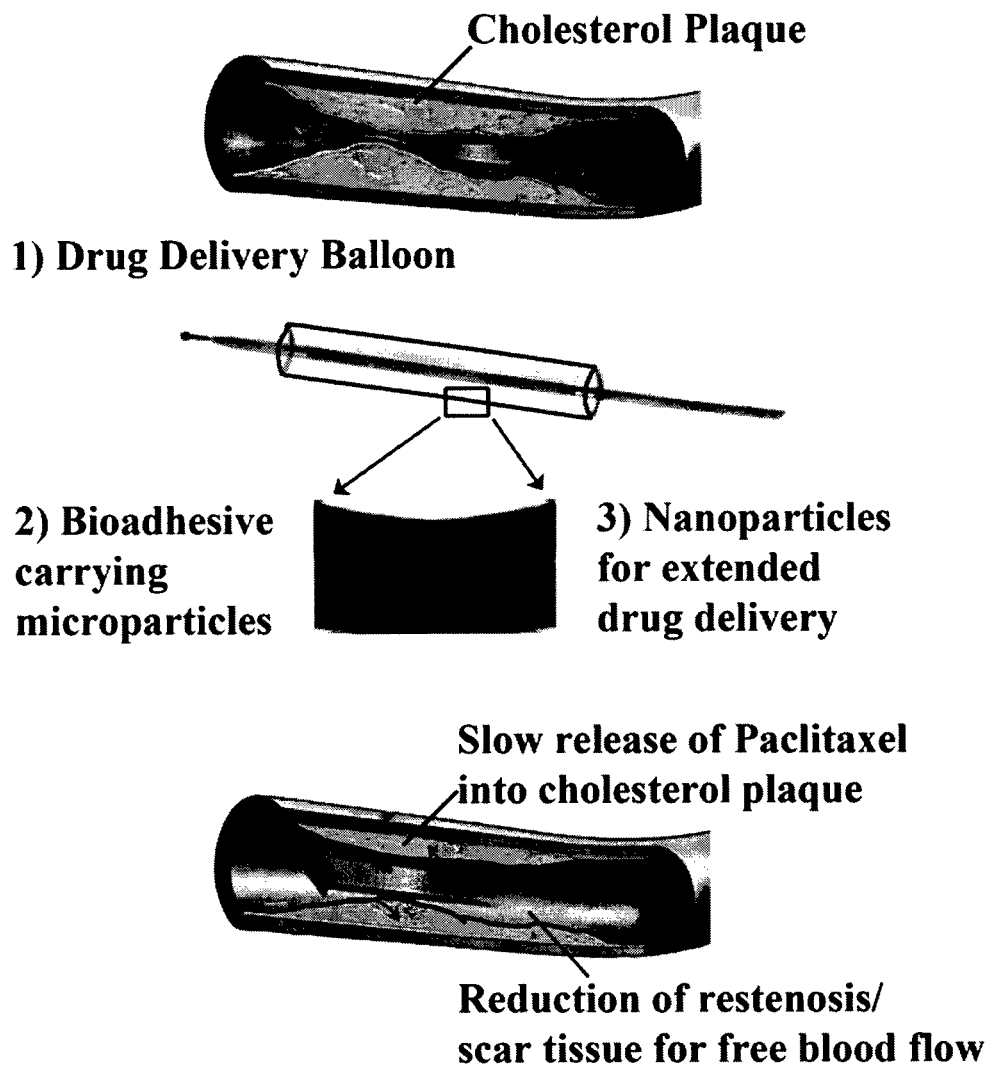
FIG. 10 shows an illustration on the use of the present device.

FIG. 10 shows an illustration on the use of the present device in one embodiment. The angioplasty balloon catheter is inserted into a blood vessel to widen the blockage caused by cholesterol plague. The angioplasty balloon is coated with a thin film (and including a bioadhesive layer in the thin film) comprising the drug particles loaded into the polymeric matrix. Nanoparticles of the drug may be used for extended delivery over a longer period of time. When the balloon is inflated, the blockage caused by the cholesterol plague is forced to open up and thereby allowing more blood flow. At the same time, the thin film contacts and adheres to the tissue even when the balloon is deflated. The thin film remains adhered to the tissue and enables localised drug delivery. Over time, the thin film degrades, dissolves and gets flushed out by the blood flow.

In one embodiment, the device of the invention comprises a bioactive agent-containing layer and an adhesive layer. The thickness of the bioactive agent-containing layer and the adhesive layer may be, for example, between 0.5 and 400 μm.

In other embodiments, the bioactive agent-containing layer is already bioadhesive so that a separate bioadhesive layer can be omitted. In this embodiment, the thickness of the bioactive agent-containing layer may be, for example, between 10 nm and 500 μm.

In further embodiments where adhesion or releasing is not needed, the device of the invention comprises only the bioactive agent-containing layer.

In other embodiments, the device of the invention comprises a release layer and the bioactive agent-containing layer and, optionally, an adhesive layer. For example, each of the respective thickness of the release layer, bioactive agent-containing layer and/or adhesive layer may be between 10 nm and 100 μm.

Alternatively, the bioactive agent-containing layer may already have release properties so that the release layer can be omitted. In such embodiments, the polymeric matrix of the bioactive agent-containing layer is already designed such that it can be readily released from the device surface, for example by means of selecting appropriate components of the polymeric matrix. The components of the polymeric matrix may comprise those of the release layer as described above. For example, the device of the invention may be used in pneumatic dilatation to dilate and delivery antibiotics to the infected area in treating esophagus strictures.

In all afore-mentioned embodiments, the bioactive agent may be encapsulated in particles that are comprised in, for example embedded in the bioactive agent-containing layer, in particular the polymeric matrix of said layer. Additional bioactive agents may also be encapsulated in particles that are comprised in the bioadhesive layer.

Further advantages of the present invention include:

(a) Drug-eluting device described above would not require a permanent medical device (i.e. bare metal stent) to remain in the obstructed artery, vein, or other transluminal pathway, where it is known that permanent medical devices can cause increase risks of thrombosis. The present invention uses a biodegradable thin film coating material with good biocompatibility. The thin film also forms strong adhesion with arterial plaques, arterial calcified plaques, arteries, veins, media arterial walls, and advententitia arterial walls;

(b) Thrombolytic therapy and anti-platelet drugs would be reduced in duration decreasing adverse risks associated with such drugs (i.e. uncontrolled bleeding);

(c) Anti-restenosis drugs would have deeper tissue penetration than that of current drug-eluting devices;

(d) Medical device would perform under same operating conditions as PTCA balloons, simplifying training and operational deployment;

(e) Re-treatment of the same obstructed artery, vein, and other transluminal pathways is possible unlike the standard therapy ('in stent' stenosis can only be treated once with another stent, or with a drug-eluting balloon). Drug-eluting device described herein has no such limitation;

(f) Localized delivery of drugs in a controlled and sustained manner is possible with present invention.

The present device may be used in the treatment of vascular diseases, such as:

(a) Coronary atherosclerosis, prevention and treatment of myocardial infarction;

(b) Carotid atherosclerosis, prevention and treatment of stroke;

(c) Peripheral artery disease, prevention and treatment of obstructed arteries in the arms and legs;

(d) Renal artery stenosis, prevention and treatment of kidney failure;

(e) Deep vein thrombosis, prevent stagnation of the blood by diminishing coagulation;

(f) Prevention and treatment of hypo/hypertension.

The present device may also be used in the treatment of non-vascular diseases, such as:

(a) Urinary tract obstruction;
(b) Urethral Strictures;
(c) Esophagus Strictures;
(d) Nasal obstruction.

In order that the invention may be readily understood and put into practical effect, particular embodiments will now be described by way of the following non-limiting examples.

EXAMPLES

Example 1

The Effect of Polyethylene Glycol Structure on Paclitaxel Drug Release and Mechanical Properties of PLGA Thin Films Thin films of poly(lactic-co-glycolic acid) (PLGA) incorporating paclitaxel have typically shown slow release rate of paclitaxel on the order of 1 μg/day·cm². For implementation on medical devices, a range of zeroth order release rate (i.e. 1-15 μg/day·cm²) is desirable for different tissues and pathologies. Polyethylene glycol (PEG) of 8k and 35k molecular weight was incorporated at 15, 25, and 50% weight ratios in PLGA containing 10% w/w paclitaxel. The mechanical properties were assessed for potential use on medical implants and the rates of release of paclitaxel were quantified in % release and the more clinically useful unit µs/day·cm². Paclitaxel quantitation was correlated to the release of PEG from PLGA to further understand its role in paclitaxel/PLGA release modulation. PEG release was found to correlate with paclitaxel release and the level of crystallinity of the PEG in the PLGA film, as measured by Raman spectra. This supports the concept of using a phase separating, partitioning compound to increase the release rates of hydrophobic drugs such as paclitaxel from PLGA films, where paclitaxel is normally homogenously distributed/dissolved. Two formulations are promising for medical device thin films, when optimized for tensile strength, elongation, and drug release. For slow rates of paclitaxel release, an average of 3.8 µg/day·cm² using 15% 35k PEG for >30 days was achieved while a high rate of drug release of 12 µg/day·cm² was maintained using 25% 8k PEG for up to 12 days.

Materials and Methods

Materials

Poly (DL-lactide-co-glycolide) 53/47 (PLGA) with intrinsic viscosity of 1.03 was purchased from Purac, Netherlands. Paclitaxel (PCTX) was purchased from Yunnan Hande Bio-Tech, China. HPLC-grade dichloromethane (DCM) and acetonitrile was purchased from Tedia, USA. Deuterated chloroform (CDCl$_3$+0.03% v/v TMS D99.8%+ silver foil) was purchased from Cambridge Isotope Laboratories, Andover, USA. Polyethylene glycol (PEG) of molecular weight of 8,000 (8k) and 35,000 (35k), and polysorbate 80 (Tween 80) were purchased from Sigma-Aldrich, Singapore. All other polar solvents used were of high performance liquid chromatography (HPLC) grade and purchased from Sigma-Aldrich, Singapore. All chemicals and materials were used as received.

Film Formulation

Polymer solutions of 20% w/v were prepared with 10% w/w paclitaxel in DCM. A typical film formulation consisted of 60 mg of PCTX and 600 mg of polymer (PLGA+0-50% PEG) in 3 mL of DCM. For example, a 25% 8k PEG/PLGA 53/47 solution was dissolved in 3 mL DCM overnight with 60 mg paclitaxel, 450 mg of PLGA 53/47 and 150 mg of 8k PEG. Film applicator height was set at 300 µm and the viscous solution was casted onto PET sheets (or Teflon™ if needed) at 50 mm/s, room temperature (RT) in a fume hood. DCM was evaporated at RT for 24 h followed by vacuum oven at 55° C. for 5 days. Punch-outs of 6 and 15 mm diameter were made for release and degradation studies respectively. The film applicator was adjusted to 500 µm to obtain 40 µm films required for evaluation of mechanical properties.

Film Wettability

Thin films (15-20 µm thick) were sliced into rectangular strips (3×1 cm) and their surface properties analyzed by contact angle (degree) and wetting tension (dyne/cm) employing a contact angle goniometer using a static sessile drop technique. The static measurements were carried out at RT using distilled H$_2$O with syringe pump rate of 5 µL/s in triplicate. An image was captured after allowing the droplet to relax (15-20 s) and analyzed with FTA32 software, version 2.0 build 276.2.

Film Mechanical Properties

The dried 40 µm thin films were sliced into rectangular strips (8×1 cm) according to ASTM D882. Each rectangular film were fixed to Instron Model 5567 grips with a load cell capacity of 10 N, pulled at rate of 5 min/min (10%/min) and analyzed with Bluehill software version 3.00. The yield strength and elongation at break were recorded in the perpendicular direction in pentuplicate. No isotropic effects on the mechanical properties were investigated.

Raman Spectroscopy

The thin films were placed under the microscope objective and laser power up to circa 10-50 mW was shone onto the surface of the sample. Raman point-by-point mapping measurements were performed on the area of 60 µm×60 µm or 100 µm×100 µm with a step size of 5 µM in both the x and y directions. The measurements were performed using a Raman microscope (InVia Reflex, Renishaw) equipped with a near infrared enhanced deep-depleted thermoelectrically Peltier cooled CCD array detector (576×384 pixels) and a high grade Leica microscope. The sample was irradiated with a 785 nm near infrared diode laser and a 50× or 100× objective lens was used to collect the backscattered light. Measurement scans were collected using a static 1800 groove per mm dispersive grating in a spectral window from 300 to 1800 cm$^{-1}$ and the acquisition time for each spectrum was around 35 seconds. Spectral preprocessing that includes spike removal and baseline correction were carried out first before the data was further analyzed using the band-target entropy minimization (BTEM) algorithm. The BTEM algorithm was used to reconstruct the pure component spectra of underlying constituents from a set of mixture spectra without recourse to any a priori known spectral libraries and has been proven well to reconstruct the pure component spectra of minor components. When all normalized pure component spectra of all underlying constituents have been reconstructed, the relative contributions of each constituent can be calculated by projecting them back onto the baseline-corrected and normalized data set. The spatial distribution of each underlying constituents can then be generated.

PEG Quantification by $^1$H NMR

One cm square films were immersed in PBS Buffer in triplicate. At predetermined time points, films were transferred to another tube containing fresh medium. After lyophilization, the powder was dissolved in 1050±10 µg (700 µL) of CDCl$_3$, vortexed, and centrifuged at 10,000 rpm for 5 min prior to transferring the supernatant into NMR tubes. $^1$H NMR spectra were recorded on Bruker Advance Spectrometer at 400 MHz using the signal of tetramethysilane (TMS) present in deuterated chloroform at 0.03% as an internal standard. $^1$H NMR (400 MHz, CDCl3, δ) 1.5-1.7 (bs, PLGA 3H, —C(=O)—CH(CH3)-O—C(=O)—CH2-O—, 3.45-3.85 (bs, PEG 4H, —O—CH2-CH2-O—, 4.6-5.0 (bs, PLGA 2H, —C(=O)—CH(CH3)-O—C(=O)—CH2-O—, 5.0-5.3 (bs, PLGA 1H, —C(=O)—CH(CH3)-O—C(=O)—CH2-O—.

In-Vitro Paclitaxel Release

The in-vitro release of paclitaxel was conducted in 2 mL of PBS/% Tween 80 release buffer (pH 7.4) at 37° C. using 6 mm punch-outs (1 punch-out/well) in triplicate. At predetermined time-points 2 mL of buffer was removed and another 2 mL replaced with PBS/Tween 80 release buffer, maintaining sink conditions throughout the release. Withdrawn aliquots (or standards/dissolutions samples) were filtered through a 0.2 µm PTFE syringe filter directly into HPLC vials and immediately capped. Paclitaxel was quantified with an Agilent Series 1100 HPLC (Santa Clara, Calif., USA) equipped with UV/Vis detector, autosampler, and column heater set to 35° C. A ZORBAX Eclipse XDB-C18 (5 µm) column of acetonitrile/water 60/40 (v/v) served as the mobile buffer, eluting the paclitaxel peak at ~5.4 minutes with a flow rate 1.0 mL/min and the UV/Vis detector recording at 227 nm. A total dissolution study of the 6 mm discs in triplicate was conducted by dissolving the films in acetone and diluting in release buffer to determine the surface concentration of paclitaxel ($\mu g/mm^2$). The solubility limit of paclitaxel in PBS/2% Tween-80 release buffer was determined to be 20 $\mu g/mL$.

Film Degradation Studies

PLGA films were incubated as described above in PBS/2% Tween-80 release buffer and then removed at predetermined time points to be thoroughly dried in a 55° C. vacuum for 5 days. Mass loss was determined gravimetrically before the films were dissolved in 1 mL chloroform, vortexed until dissolved, and syringed through 0.2 $\mu m$ filters into immediately capped HPLC vials. Weight average molecular mass ($M_W$) of polymers were determined by size exclusion chromatography (SEC) using a Shimadzu LC-20AD HPLC equipped with R1 detector and column heater set at 35° C. Low polydispersity polystyrene standards (Fluka) from 580-400,000 kDa were used for calibration of three linear PLgel (5 $\mu m$) mixed C columns (Varian, Singapore) HPLC grade chloroform was used as mobile phase at flow rate of 1.0 mL/min. A differential scanning calorimeter (Q500 DSC, TA Instruments) was used to determine the thermal transitions of the films as a function of degradation time. The samples were heated from −30° C. to 80° C. and cooled to −30° C. at a rate 20° C./min for two consecutive cycles, under pure dry nitrogen at a flow rate of 50 mL/min. The glass transition temperature ($T_g$) was determined by the signal minima/maxima from the second DSC thermogram obtained, analyzed with TA Universal Analysis software.

Film Surface Topography

Degraded PEG incorporated PCTX-PLGA films were coated with platinum for 50 s under a chamber pressure of less than 5 Pa at 20 mA using JEOL JFC-1600 Auto Fine Coater, Japan. Secondary electron images were acquired at 5.0 kV, 12 $\mu A$, at a working distance of 8 mm under the Field Emission Scanning Electron Microscopy (FESEM) (JEOL JSM-6340F, Japan).

Results

Surface Hydrophilicity

The surface properties of the PLGA 53/47 films were characterized using contact angle and wetting tension measurements with distilled water. Table 1 displays PLGA 53/47 (neat), with 10% paclitaxel, and then mixed with 8k and 35k PEG. Knife casted PLGA 53/47 (neat) had similar values to that of spin-coated PLGA 75/25 and solution casted PLGA 70/30 of 73±2, 76.1±0.3, and 78 degrees, respectively. Addition of 10% lipophilic paclitaxel raises the contact angle by 16 degrees and decreases the wetting tension, indicating an increase in surface hydrophobicity. Addition of both PEGs at 15% w/w concentration decreased the contact angle from 89±3 to ~50 degrees and improved the wetting tension by an order-of-magnitude. Increasing the PEG concentration to 25% sees no further drop in contact angle, whereas at 50% of PEG, the contact angle decreased by another 10%. For the PEG incorporated films, it was noted that the contact angle continued to decrease over time (on the order of minutes). For reproducible evaluation, all image photos were captured immediately after the water droplet was static, and ripple perturbations had subsided (15-20 s). For comparison, similar contact angles were seen with PLGA surface treatments of chitosan/gelatin coating and oxygen plasma treatment.

The PEG % also had an effect on the adhesion of the PLGA films to the substrate used for film casting. When the films were cast on borosilicate glass plates or on polyethylene teraphthalate sheets, the films could be peeled off with a metal spatula for the 15% and 25% PEG formulations. PLGA (neat) or with 10% paclitaxel could not be removed from these substrates—Teflon™ plates had to be utilized. 50% PEG films were brittle and could be flaked off the surface, but not peeled.

TABLE 1

Water-in-air $dH_2O$ Contact Angles and Wetting Tension for treated PLGA films.

| | $dH_2O$ Contact Angle (deg) | Wetting Tension (dyn/cm) |
|---|---|---|
| PLGA 53/47 | 73 ± 2 | 5 ± 2 |
| w/10% paclitaxel | 89 ± 3 | 2 ± 2 |
| w/15% PEG 8k | 49 ± 2 | 52 ± 2 |
| w/25% PEG 8k | 49 ± 1 | 47 ± 2 |
| w/50% PEG 8k | 37 ± 1 | 59 ± 1 |
| w/15% PEG 35k | 51 ± 2 | 46 ± 3 |
| w/25% PEG 35k | 49 ± 2 | 48 ± 2 |
| w/50% PEG 35k | 38 ± 2 | 58 ± 2 |
| PLGA 75/25 | 76.1 ± 0.3 [35] | NR |
| w/surface modified chitosan and gelatin | 51.5 ± 0.7 [35] | NR |
| PLGA 70/30 | 78 [36] | NR |
| w/$O_2$ plasma treatment | 45 [36] | NR |

NR = Not Reported.

Raman Spectra

Figure 1:
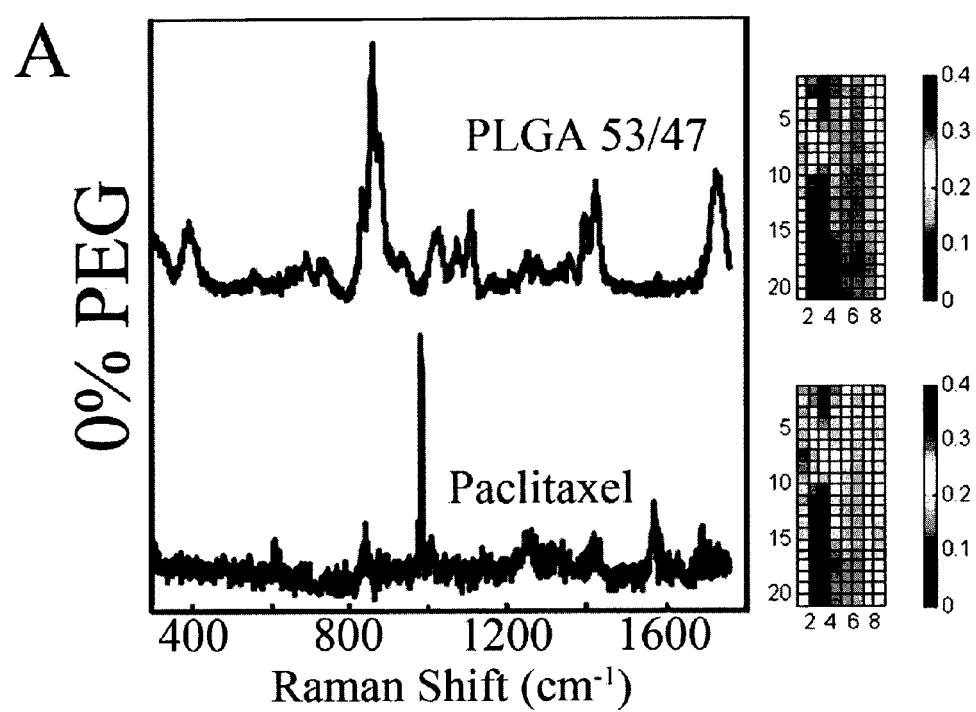
FIG. 1 shows Raman mapping of A) 10% paclitaxel/PLGA 53/47 B) 15% 8k PEG/PLGA 5347 w/paclitaxel C) 15% 35k PEG/PLGA 53/47 w/paclitaxel.
Figure 1:
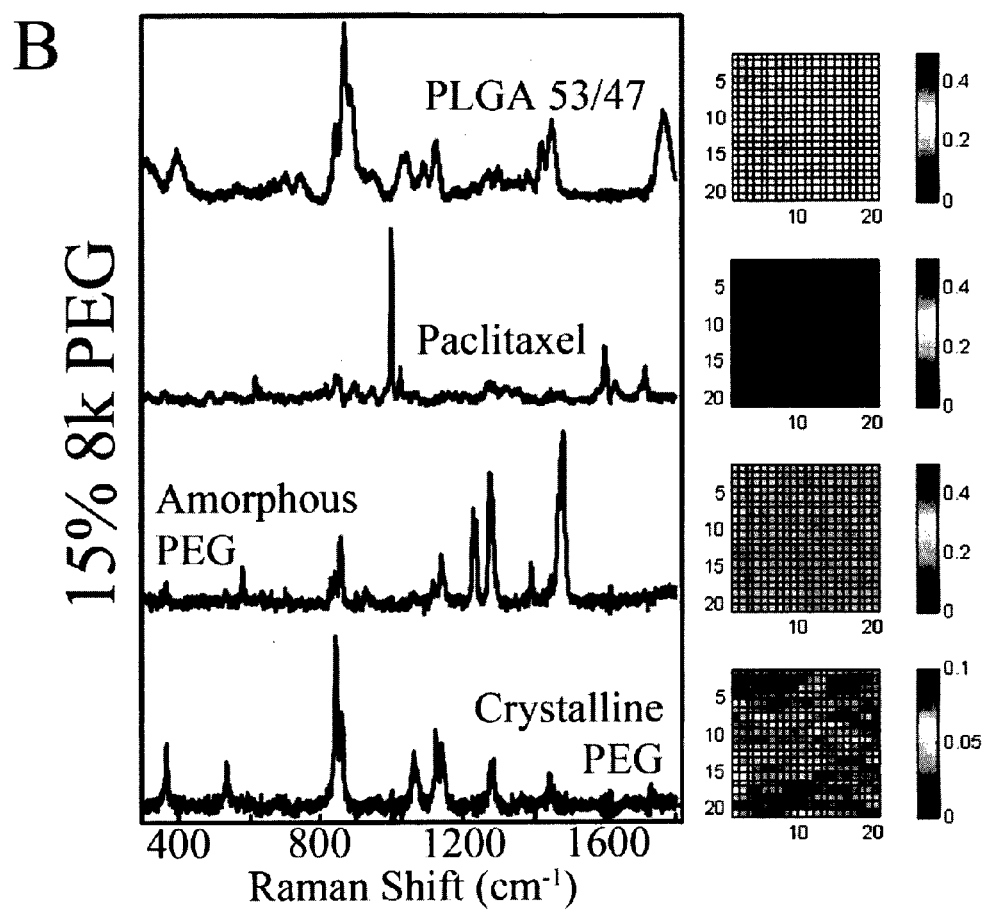
Figure 1:
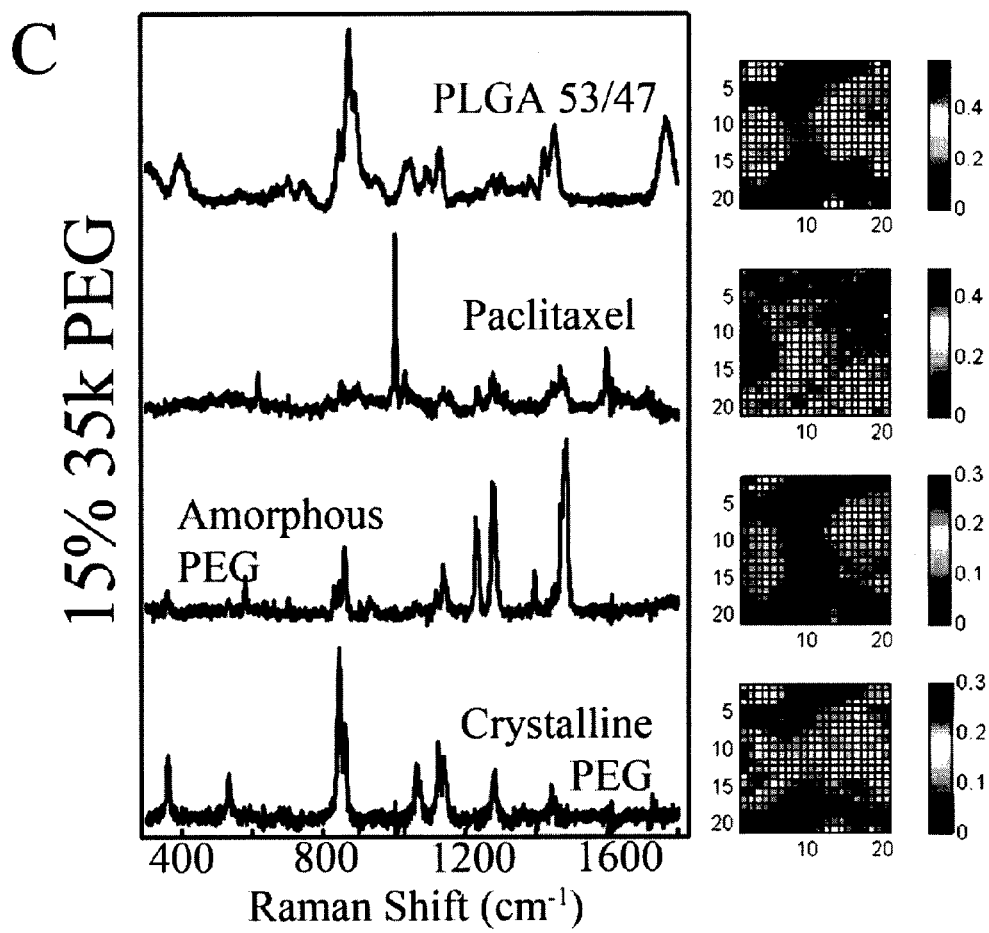

Pre-processed Raman mapping data from 10% paclitaxel/PLGA, 15% 8k PEG/PLGA, and 15% 35k PEG/PLGA were subjected to BTEM analysis in order to reconstruct the underlying pure component spectra and their associated spatial distributions, which are displayed in FIG. 1. The reconstructed pure component spectral estimates via BTEM were then compared to known spectral libraries. It was found that the spectral estimates corresponded to the PLGA 53/47, paclitaxel, amorphous, and crystalline PEG. The BTEM estimate of PLGA 53/47 shows strong and prominent Raman peaks at 846, 873, 890 $cm^{-1}$ and some additional peaks at 1046, 1095, 1130, 1425, 1454, and 1768 $cm^{-1}$. The BTEM estimate of paclitaxel shows strong and prominent Raman peaks at 1002 $cm^{-1}$ and some additional bands at 618, 1028, and 1602 $cm^{-1}$. The BTEM estimates of amorphous and crystalline PEG show prominent Raman peaks at 582, 859, 1139, 1231, 1395, 1469, 1479, 1486 $cm^{-1}$ and 363, 534, 844, 860, 1063, 1124, 1140, 1280 $cm^{-1}$ respectively. The prominent Raman peaks of crystalline PEG at 844 and 860 $cm^{-1}$ has been previously used to differentiate the PEG crystalline phase from its amorphous phase. In the present example, the crystalline phase of PEG was detected in both 15% 8k and 35k PEG films. This indicates that the recrystallization of amorphous PEG has occurred for both systems. However, the ratio of recrystallization of amorphous PEG was somewhat different between these two systems. As shown by the intensities of their score images, the recrystallization of amorphous PEG was more advanced for 15% 35k PEG system compared to 15% 8k PEG.

The Raman mapping and subsequent BTEM analysis also provide the spatial distributions of each constituent used in these systems. As can be seen in FIG. 1A, PCTX was distributed homogeneously within PLGA. In FIG. 1B (15% 8k PEG), again it can be observed that PCTX is also distributed homogeneously. Closer look also reveals that uniform and homogeneous distribution was observed for PLGA 53/47, PCTX, and amorphous PEG, but not for crystalline PEG, as the recrystallization of amorphous PEG may not occur in a spatially homogenous way but more discretely. FIG. 1C (15% 35k PEG), on the other hand, shows that the distribution of all constituents was not uniform. Non-uniform distributions in PEG and paclitaxel became visually apparent at 15% 35k PEG and at the 25% 8k and 35k PEG films (data not shown). Crystallization of amorphous PEG was more pronounced, and paclitaxel was found to preferentially co-localize in the crystalline PEG regions. In the 50% PEG formulations, the brittle films were composed of mostly crystallized PEG.

Mechanical Properties

Figure 2:
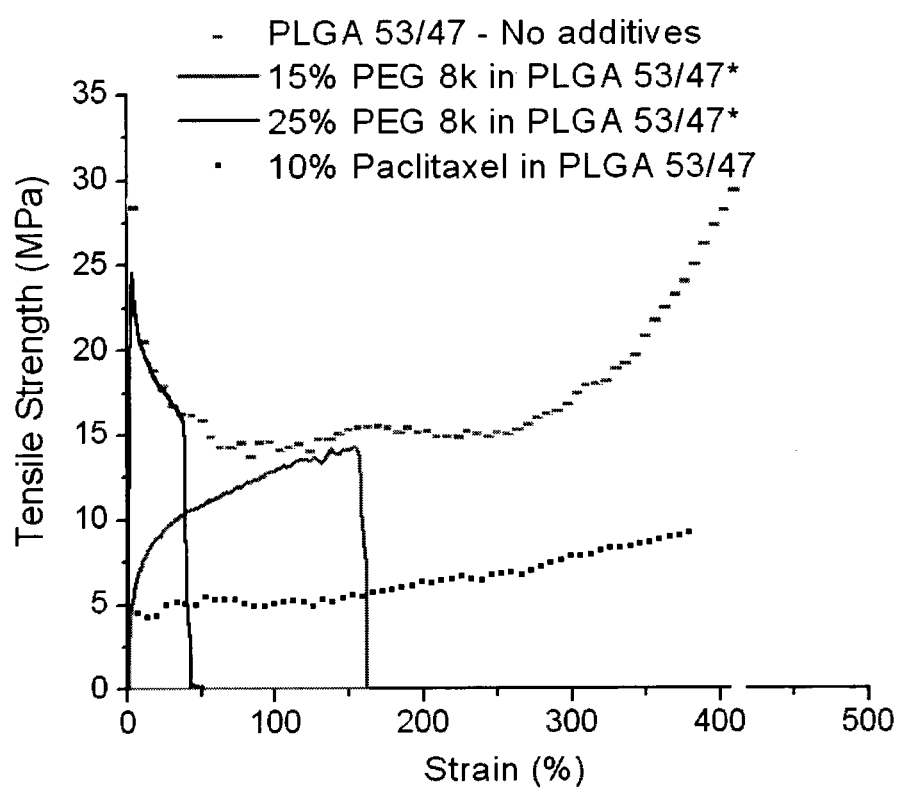
FIG. 2 shows stress vs. strain of PLGA 53/47 (neat), PLGA 53/47 w/10% paclitaxel, and 15%, 25% 8k PEG PLGA 53/47 thin films. *PLGA 53/47 contains 10% paclitaxel.
Figure 3:
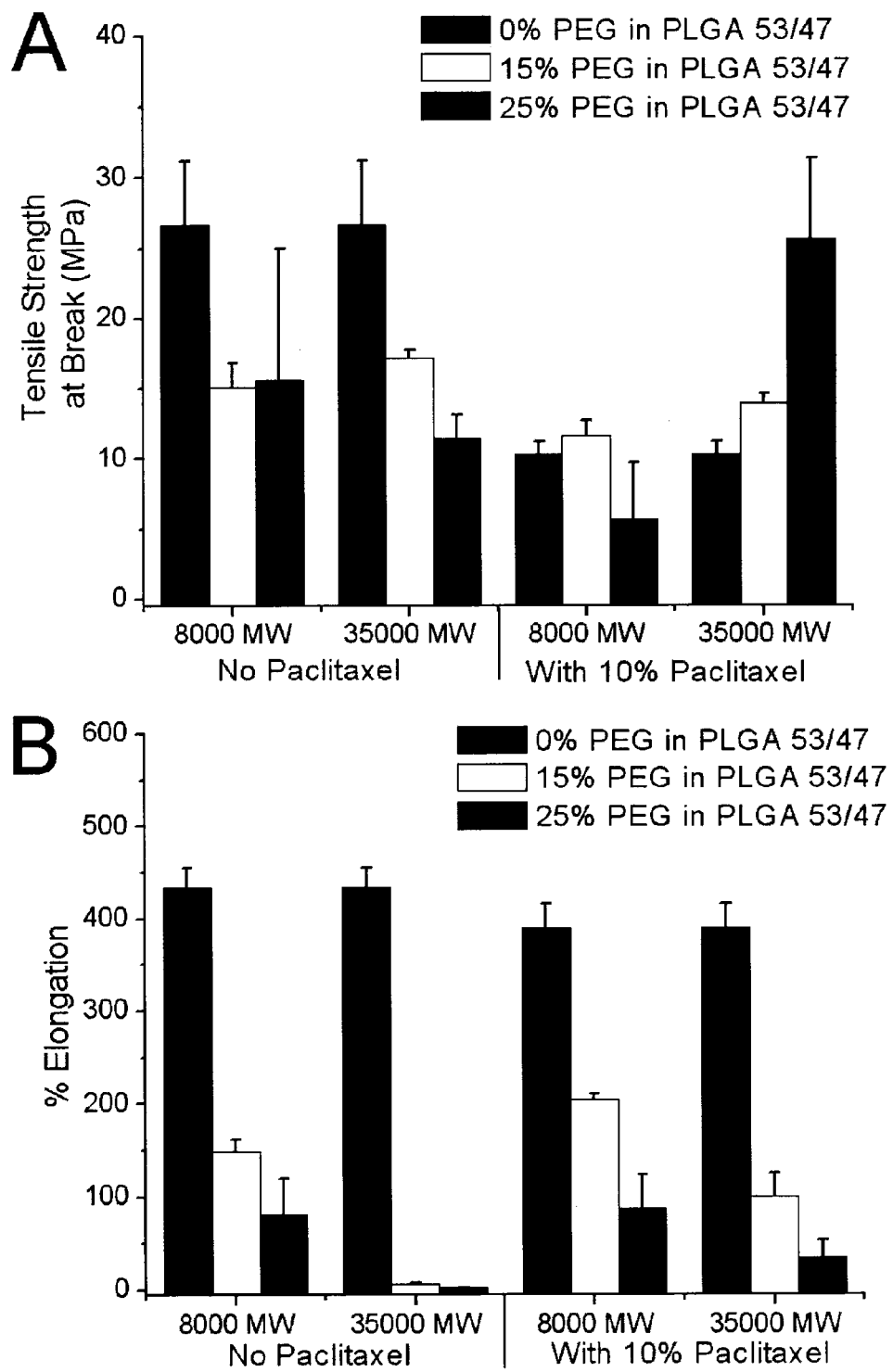
FIG. 3 shows mechanical properties of PLGA/PEG thin film with respect to A) Tensile Strength at Break B) % Elongation.

To determine the PLGA blended films potential in expanding medical devices, the mechanical properties of elongation and tensile strength at break were determined using 40-50 μm×1 cm×8 cm strips, with 5 cm of film between the tensile grips at 0% strain. FIG. 2 displays the stress vs. strain curves for four formulations: PLGA (neat), w/10% paclitaxel, w/15% PEG 8k and w/25% PEG 8k (both PEG formulations include 10% w/w paclitaxel). As previously mentioned, 50% PEG formulations were brittle and not sufficiently ductile for tensile analysis. Addition of 10% paclitaxel to PLGA (neat) caused a 2.5 fold reduction in tensile strength at break, probably due to the fact that paclitaxel is crystalline at RT. Addition of PEG reduced the PLGA (neat) break by 35-40% and elongation was even further reduced to 75% for 8k PEG and 95% for 35k PEG. Upon addition of PEG, PLGA w/paclitaxel retained more break strength and elongation than PLGA (neat). Overall, the 35k PEG increased the break when added to the PLGA w/paclitaxel, but elongation was hindered (see FIGS. 3A and 3B). Elongation was greater for 8k PEG compared to that of the 35k, but still was 2-5 fold less than the PLGA with or without paclitaxel.

Paclitaxel Release from PLGA 53/47 Thin Films

Table 2 lists the matrix properties of the films measured for paclitaxel release. The target thickness was between 15-20 μm, which maintains flexibility and was estimated to allow enough drug loading for 30+ days of release. Viscosity differences between PLGA and PEG accounted for the differences in thickness and paclitaxel surface concentration. The 10% paclitaxel was calculated based on the weight of combined PEG and PLGA. As PLGA 53/47 was replaced with increasing amounts of PEG, the solutions became less viscous and dried to thinner films, affecting the paclitaxel surface concentrations. Thus, the paclitaxel surface concentrations were quantified and listed in Table 2, with the results exhibiting higher loading for the 35k PEG formulations.

As a control, 10% paclitaxel with no PEG was prepared to compare the effects of increasing % PEG in PLGA. The hydrophobic paclitaxel was slowly released at an average of 2.2 μg/day·cm$^2$, which accounted for 17% of the total after 33 days (see FIG. 4A, 4B). Addition of 15% 8k PEG increased this to a meager 3.5 μg/day·cm$^2$ for a total of 26% in the same time period. Neither of these formulations displayed any burst release. With 25% 8k PEG, a burst of 56±12 μg/cm$^2$ (17±4%) was released in 1 hr and 96±20 μg/cm$^2$ (29±6%) after 1 day. This formulation was observed to have the best overall profile for paclitaxel release of any of the films analyzed. After day 1, ~12 μg/day·cm$^2$ of drug was released on average for the next 12 days before the release decreased, amounting to 76±11% of the total drug content after 33 days. The 50% 8k exhibited little controlled release with an 80% burst of drug after the first day.

Figure 5:
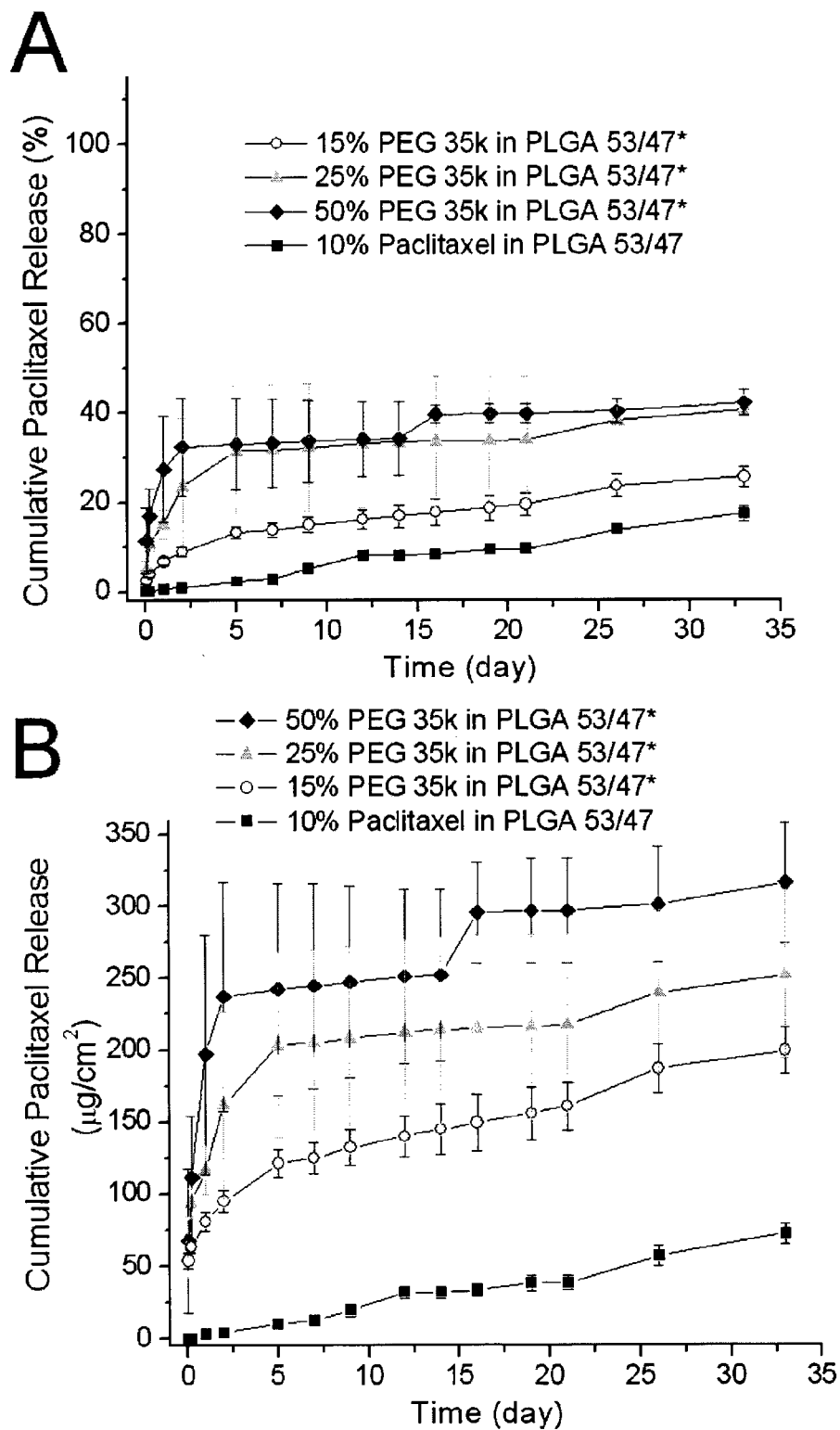
FIG. 5 shows A) % Cumulative release of paclitaxel in 35k PEG/PLGA films B) µg/cm$^2$ cumulative release of paclitaxel in 35k PEG/PLGA films. *PLGA 53/47 contains 10% paclitaxel. All films are 10-20 µm in thickness.

An increase in the MW PEG had a result contradictory to that of the smaller 8k PEG. At the lower concentration of 15% 35k PEG, 7% burst was quantified after the first day, and then a long sustained release was demonstrated for the next 30 days at an average of 3.8 μg/day·cm$^2$, as seen in FIGS. 5A and 5B. This was the longest sustained release of any of the formulations. An increase in % PEG merely increased the burst over 2 days, and then exhibited nearly the same flat release profile. From day 2 to 33, the amount of diffusion based release was inverse to the amount of 35k PEG with 104, 91, and 80 μg/cm$^2$ paclitaxel for 15, 25, and 50% 35k PEG films. The integrity of the films was noticeably worse with the 25% and 50% PEG, as considerable release standard deviation was noticed from the 6 mm punch-outs. Subsequent analyses from the same film stock did not improve on the release precision.

TABLE 2

Figure 4:
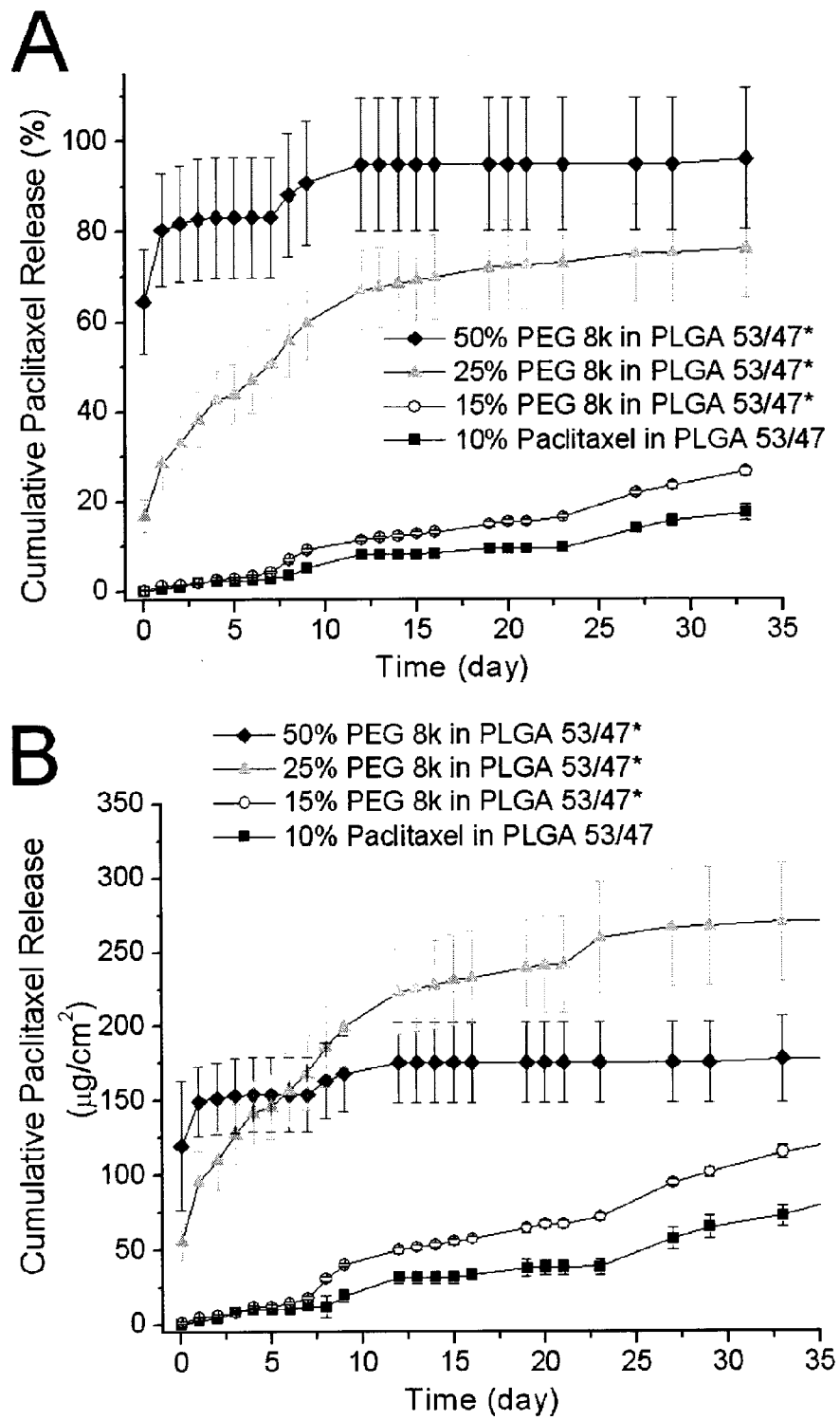
FIG. 4 shows A) % Cumulative release of paclitaxel in 8k PEG/PLGA films B) µg/cm$^2$ cumulative release of paclitaxel in 8k PEG/PLGA films. *PLGA 53/47 contains 10% paclitaxel.

Matrix properties of PLGA 53/47 thin films in FIGS. 4. and 5.

| Film composition | Thickness (μm) | Paclitaxel Surface Concentration (μg/mm$^2$) | % PEG (by $^1$H NMR) |
|---|---|---|---|
| 10% Paclitaxel PLGA 53/47 | 16 ± 2 | 4.2 ± 0.2 | 0 |
| w/15% 8k PEG | 16 ± 3 | 4.3 ± 0.8 | 16 ± 1 |
| w/25% 8k PEG | 16 ± 3 | 3.3 ± 0.5 | 25 ± 1 |
| w/50% 8k PEG | 13 ± 5 | 1.9 ± 0.2 | 50 ± 3 |
| w/15% 35k PEG | 21 ± 6 | 6 ± 2 | 16 ± 1 |
| w/25% 35k PEG | 19 ± 5 | 5 ± 2 | 26 ± 1 |
| w/50% 35k PEG | 18 ± 3 | 7 ± 2 | 51 ± 3 |

Release of PEG from PLGA 53/47 and Mass Loss Composition

Figure 6:
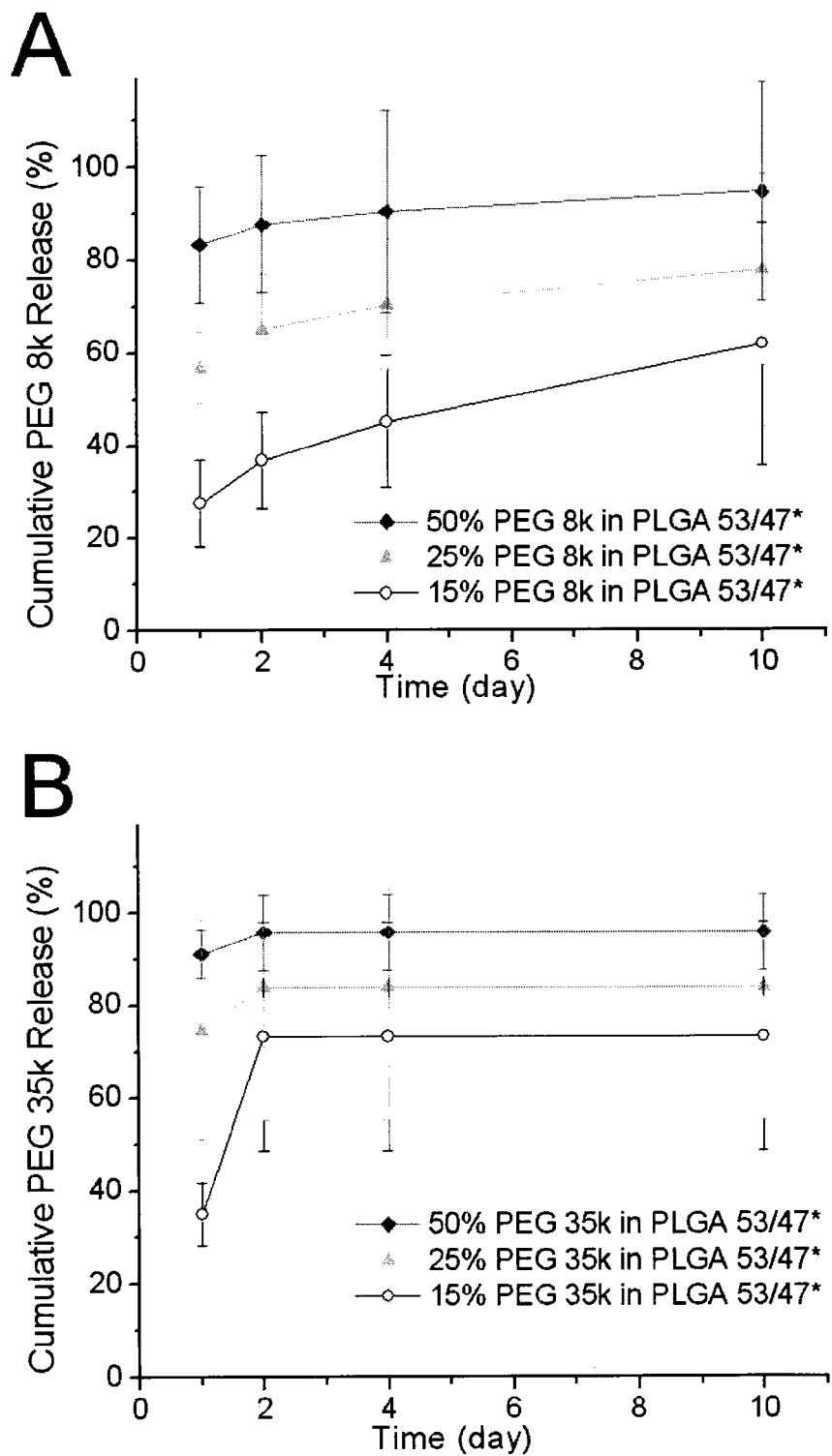
FIG. 6 shows % cumulative release of PEG in A) 8k PEG/PLGA and B) 35k PEG/PLGA. *PLGA 53/47 contains 10% paclitaxel. All films are 10-20 µm in thickness.

The % mass remaining of the PLGA/PEG films was followed at 4, 10, 15, and 21 days in 37° C. PBS/2% Tween 80 release buffer. After the specified time, films were dried and gravimetric weight measurements were recorded to determine the mass of film remaining. On a separate set of samples, the release of PEG and PLGA 53/47 was followed by NMR quantitation (See Materials and Methods). This data was merged with the HPLC paclitaxel quantitation to determine amount of PEG dissolution and soluble/degraded PLGA 53/47. FIG. 6A and FIG. 6B plot % cumulative PEG release vs. time for 8k and 35k PEG, and Table 3 gives the % composition of PEG, paclitaxel, and PLGA 53/47 at 4 and 10 days. Day 15 and 21% mass remaining data displayed only trace increases from day 10 (data not shown).

The largest decreases in residual mass were seen with the highest amounts of % PEG, as expected. An analysis of the mass loss composition and PEG release reveals the large effect that both amphiphilic PEGs had on the release of paclitaxel in the first four days. For example, addition of 25% 8k and 15% 35k increased the paclitaxel release an order of magnitude (~100 μg/cm2) after four days, versus that of the no-PEG control.

Burst and sustained release of paclitaxel formulations correlated to the corresponding PEG release as well. For example, the 35k PEG formulations showed no sustained release of PEG after two days—only a burst was displayed (see FIG. 6B). Within the burst time period of 2 days, the majority of the paclitaxel was released concurrently (in the 30 day time frame). After the PEG burst, the paclitaxel release rate was similar to the non-PEG modified film of 10% paclitaxel/PLGA. The 8k PEG formulations were observed to have two small sustained PEG release profiles at the 15% and 25% PEG films, in which paclitaxel release was 2× and 9.5× (at Day 10) that of non-PEG modified film of 10% paclitaxel/PLGA, respectively. The 15% 8k PEG, with the lower PEG crystallinity, had virtually no burst release, while the 25% 8k did, with a more dramatic release of paclitaxel. This suggests that the proportion of PEG crystallinity can influence paclitaxel release.

TABLE 3

Composition of mass loss at 4 and 10 days in PBS/2% Tween-80 release buffer.

| Mass Loss Composition | Total Loss (µg/cm²) | Day 4 Ratio of Released PEG/PCTX/PLGA % (µg/cm²) | | | Total Loss (µg/cm²) | Day 10 Ratio of Released PEG/PCTX/PLGA % (µg/cm²) | | |
|---|---|---|---|---|---|---|---|---|
| 10% Paclitaxel/PLGA | 60 | 0(0) | 15(10) | 85(50) | 70 | 0(0) | 28(20) | 72(50) |
| w/15% 8k PEG | 250 | 74(186) | 4(10) | 20(50) | 340 | 75(255) | 11(39) | 15(50) |
| w/25% 8k PEG | 630 | 71(448) | 21(135) | 8(50) | 730 | 68(496) | 26(189) | 7(50) |
| w/50% 8k PEG | 1210 | 83(1007) | 12(151) | 4(50) | 1270 | 83(1054) | 13(163) | 4(50) |
| w/15% 35k PEG | 330 | 53(176) | 33(108) | 15(50) | 360 | 53(176) | 33(108) | 15(50) |
| w/25% 35k PEG | 580 | 60(346) | 31(180) | 9(50) | 600 | 58(346) | 34(202) | 8(50) |
| w/50% 35k PEG | 1310 | 78(1020) | 18(240) | 4(50) | 1320 | 77(1020) | 19(247) | 4(50) |

PCTX = paclitaxel.
Total Loss/cm² (ΔM) = $M_o/cm^2 - M_t/cm^2$ where $M_o$ was initial mass and $M_t$ was the dried $M_o$ mass after t days in 37° C. PBS/2% Tween 80 release buffer.
Standard deviations for all values are ≤10%.
Ratio of released of PEG, paclitaxel, and PLGA was calculated from the soluble fractions by NMR (PEG and PLGA) and HPLC (paclitaxel).

PEG Effects on PLGA Degradation

Figure 7:
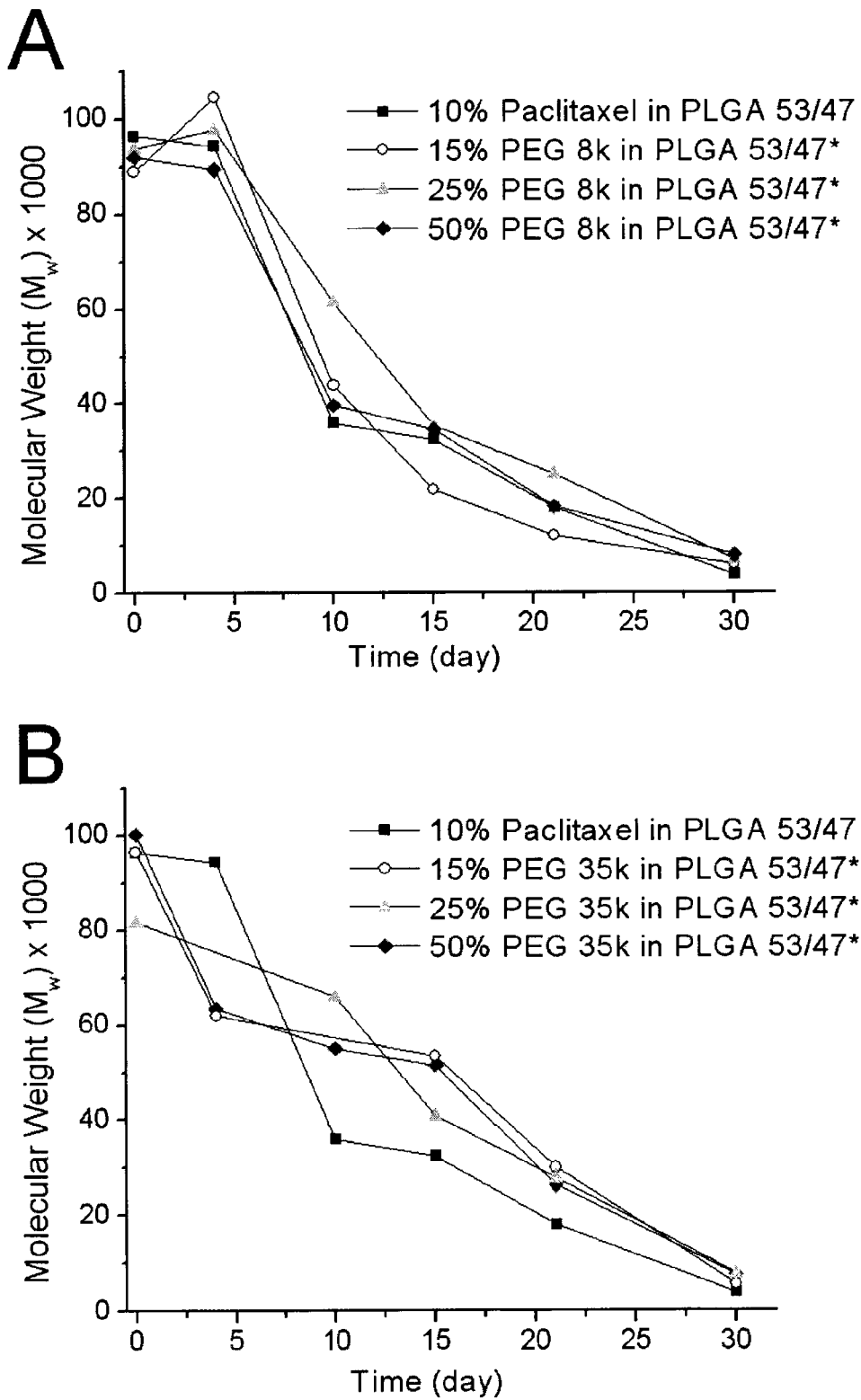
FIG. 7 shows molecular weight decay for A) 8k PEG/PLGA and B) 35k PEG/PLGA. $M_w$, weight average molar mass. *PLGA 53/47 contains 10% paclitaxel. All films are 10-20 µm in thickness.

The MW of the PLGA polymers was expected to decrease faster for the higher % PEG/PLGA, due to the higher wetting tension and osmotic gradient (from the internal PEG bound within the PLGA matrix). When including the typical error of GPC analysis to be around 10-20% for MW, the 8k PEG does not display any accelerating or retarding of the polymer degradation—the degradation trend in the 10% paclitaxel/PLGA formulation was consistent for all 8k PEG formulations in FIG. 7A. For the 35k PEG, a slight retardation of the degradation was noticed overall, as seen in FIG. 7B. After day 10, all three films continued to be have higher $M_w$ averages for the next 4 time points, or 20 days overall, but this could be due to the higher MW fractions inherent in PEG 35k, that overlap the lower MW fractions in PLGA 53/47 (intrinsic viscosity of 1.03, ~150k/142k $M_w/M_n$). But no trend was noticed with the three 35k PEG containing films.

Surface Topology and PEG Leaching

Figure 8:
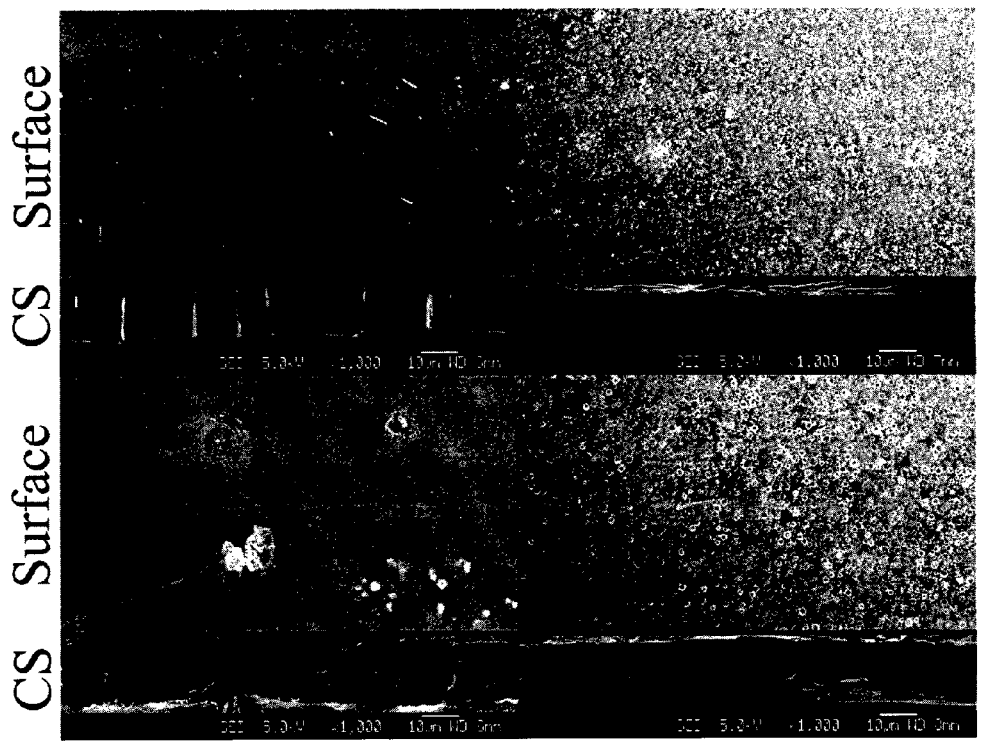
FIG. 8 shows scanning electron microscopy (SEM) of in PLGA 53/47 at A) day 0, B) day 10, C) w/15% 8k at day 0, and D) w/15% 8k at day 10. *PLGA 53/47 contains 10% paclitaxel. All films are 10-20 µm in thickness.

The surface topology of 15% 8k PEG was visualized at 1000× magnification with the aid of a field emission scanning electron microscope. Formulations without PEG appear smooth with occasional serrations caused by artifacts in the knife caster. These films do not form pores before or after as seen in FIGS. 8A and 8B. FIG. 8C gives a typical PLGA film incorporating PEG (15% 8k) before buffer immersion and 10 days after. Even before immersion and polymer degradation, the surface was 'rough' with nano-to-micro size pores, that are likely to be caused by phase separation of the PEG, even though the films appears homogenous with the Raman spectroscopy (see FIG. 8A). As degradation proceeds within the aqueous buffer and both amorphous and crystalline PEG dissolve, the pores grow larger and are likely to be the first points of PLGA degradation, as seen in the larger pores sizes in FIG. 8D.

Discussion

PEG MW and Paclitaxel Release

By incorporating low and high MW PEG into 10% paclitaxel PLGA films, release of paclitaxel could be correlated with wettability, crystalline PEG, mechanical properties, and MW loss. Earlier work with low-MW PEG showed some limitations. For example, Jackson et al. (*Int J Pharm* 2004; 283:97) used 10% 350 MW methoxy-poly (ethylene glycol) in the 100 µm PLGA films containing from 5-30% w/w paclitaxel. The 15% paclitaxel loaded film in Jackson et al. study was found to have a release of ≤3 µg paclitaxel/day (or about 0.4%/day). The 350 MW methoxy-polyethylene glycol itself was leached out much faster as 75% (or 375 µg from a 5 mg film) of it was depleted within 72 h, similar to our present results for the 50% 8k and 35k PEG, although no paclitaxel release was associated with this burst of low MW methoxy-polyethylene glycol. Compared to the 350 MW PEG above, the higher MW 8k and 35k PEG in this study had a more impressive effect on the paclitaxel release, which allowed faster rates of paclitaxel delivery with less paclitaxel loading overall. Higher PEG MW may have a larger paclitaxel loading ratio, increasing the overall solubility in aqueous solution. Paclitaxel partitioning molecules such as PEG and cyclodextrin have been observed to increase the solubility of paclitaxel, most likely by both non-specific and specific binding, respectively.

Co-localization of Crystalline PEG and Paclitaxel

The addition of PEG to both biodegradable polymers and non-degradable polymers has confirmed its usefulness in forming pores and increasing the overall porosity, but this can be polymer dependent. For example, when poly-caprolactone (PCL) films are mixed with PEG, 2-5 µm droplets are formed throughout the film, where the size of the droplets was inversely correlated with the MW of the blended PEG—larger the MW, the smaller the pores. The PLGA/PEG blends used here exhibited a different profile. Spatial distributions of paclitaxel and 15% 8k MW PEG was uniform, but spectral peaks of 800-860 $cm^{-1}$ indicated crystalline PEG among the more common amorphous state as seen from FIG. 1B, but also become apparent at the sub-micron level in FIG. 8A. Phase separations in PEG with co-localized paclitaxel became apparent at micro-scale at 15% 35k PEG (FIG. 1C). The PEG release in FIG. 6A and FIG. 6B, and subsequent composition analysis presented that the films were not leaching PEG in one large bolus for both molecular weights. The 15% 8k exhibited a more gradual PEG release, whereas the other formulations exhibited some level of burst release. The gradual release of PEG in the 15% 8k formulation with a small burst of PEG release did not correlate with a considerable raise in paclitaxel release kinetics (2× vs. 10% paclitaxel/PLGA).

The paclitaxel in the PLGA films with no PEG added appears to be homogenously distributed, which accounts for the slow, diffusion based release. When the PEG was added in, it was initially homogenously distributed at the 15% PEG concentration; physically present as amorphous PEG in the Raman mapping of FIG. 1, with traces of crystalline PEG observed. Paclitaxel was still homogenously distributed here as well, meaning that there is no partitioning into the PEG (there is probably no phase separation at this loading of PEG). For the 15% 8k PEG, a burst of PEG release (~25% of total) was seen, but this did not correlate with any burst of paclitaxel—the rate of release was equivalent to that of the no-PEG control. The PEG burst likely originates from the amorphous PEG at the PLGA surface—and since paclitaxel was still uniform in the PLGA, the amorphous PEG did not enhance its release.

Dissolved Crystalline PEG Associated with Increased Paclitaxel Burst/Release

The 15% 35k, 25%, and 50% PEG formulations demonstrated high burst release rates for the PEG and paclitaxel, and this was due to the probable formation of crystalline PEG at this higher PEG MW and higher PEG concentration. FIG. 1C exhibits the phase separations of crystalline PEG, paclitaxel, and PLGA. Paclitaxel was co-localizing and concentrating within these crystalline PEG phases, and was no longer homogenously distributed throughout the PLGA/PEG film, although it was still present in the PLGA/amorphous PEG phase. These crystalline PEG regions likely dissolve within the first few days, as seen in the increased % PEG dissolved in FIG. 6. With a portion of the paclitaxel co-localized in these fast dissolving crystalline-PEG regions, it was released at a much faster rate as well. After the crystalline PEG dissolved away, the paclitaxel release rate reverted to the diffusion based rate seen with the homogenously distributed paclitaxel of PLGA/amorphous PEG. Differential scanning calorimetry supports this observation, as no crystalline PEG was present in PEG/PLGA films after 4 days of release buffer immersion (data not shown).

The presence of crystalline PEG controls the rate of paclitaxel release, and should be optimized when using PEG additives. If the added PEG is amorphous, it does not alter the rate of release from the matrix polymer, as seen in FIG. 4. At the other extreme, a substantially high level of crystalline PEG yielded an unsustainable high initial rate (aka burst release) such as seen for both the 50% 8k and 35k formulations. In our study, the crystallinity was controlled by the amount of PEG and its MW. Other studies have revealed that rate of solvent evaporation can control the amount of crystalline PEG, and subsequently the phase separation pore size in the film. Faster evaporating dichloromethane (used in our films, by 40° C.) was seen to have less crystallinity than the higher boiling acetone (57° C.). Lin and Lee (*J Control Release* 2003; 89:179) used this technique to increase the film pore size as the crystalline PEG was immediately dissolved.

The MW degradation supports the PEG-crystalline/paclitaxel phase separation modulated release, as the addition of PEG had only modest influence on the PLGA autocatalytic chain scission. It cannot be said that the amorphous PEG remaining hydrated the PLGA matrix faster on a time scale relevant to PLGA polymer cleavage. With the films in the 15-20 μm thickness, hydration of the samples would be quick regardless of the additive. This has also been demonstrated with other hydrophilic additives in PLGA, such as poly(vinyl alcohol) grafts.

Raman Microscopy Multivariate Analysis Compared to Coherent Anti-stokes Raman Scattering Kang et al. (*J Control Release* 2007; 122:261) have also used a Raman microscopy technique, coherent anti-stokes Raman scattering (CARS), to visualize PEG 2k/paclitaxel domains in PLGA films. However, our Raman technique is quite different. CARS uses non-linear optical imaging whereas our present Raman approach is based on linear optical imaging. Although CARS is a much faster technique compared to the conventional Raman microscope, it also has some drawbacks when used to generate the spatial distribution of PEG, PLGA, and paclitaxel. The approach used here was based on a multivariate analysis or full-spectral range analysis from 300 to 1800 cm$^{-1}$ whereas the CARS images of PEG, PLGA, and paclitaxel were generated either from particular peak positions (i.e. 2890 cm-1 for PEG and 2940 cm-1 for PLGA) or from a much shorter range of certain spectral band (i.e. 3060-3090 cm-1 for paclitaxel). Such overlapping of spectra may yield greater uncertainty in the final spatial distributions.

Effects of PEG/Paclitaxel Phase Separations on Film Material Properties

When comparing the two molecular weight PEGs, it can be assumed that the 35k PEG had a more crystalline profile in PLGA than the 8k, as it is not likely to diffuse faster than a smaller MW. While this may have increased paclitaxel burst rates, it was detrimental to the material properties, as film elongation was more compromised in 35k PEG. In a medical device usage, these parameters would need to be carefully optimized. Crystalline PEG/paclitaxel phase separations were also present at the sub-micron level, as visualized by the sub-micron pits and pores present in the FIG. 8 SEM results. If the sub-micron phase separations were distributed over the entire film, the film would appear homogenous on Raman mapping, but the material properties would still be affected, as we see for the 15% 8k PEG formulations when compared to the (neat) PLGA films.

When blended separately with PLGA, PEG and paclitaxel had deleterious effects on both the tensile strength and elongation. This contradicts results published elsewhere, that small 350 MW PEG increases PLGA elongation. This likely is MW dependent, as more elongation was seen for 8k than the 35k PEG. The elongation was greater than 20%, which would make them a potential film formulation for non-compliant drug eluting angioplasty balloons, which stretch from 10-20% at maximum inflation pressure. When paclitaxel and PEG were combined together, the deleterious effects were additive for tensile strength. The formation of the crystalline PEG pores probably accounts for the reduced structural integrity. However a substantial amount of elongation was recovered when paclitaxel was blended into the PEG/PLGA thin films. It was most dramatic for the 35k PEGfilms, adding an order of magnitude amount of elongation from no paclitaxel, to films containing 10% paclitaxel. The addition of paclitaxel probably reduces the ratio of crystalline to amorphous PEG. Addition of PEG also added a practical usefulness to the films—it changed the surface energy to a more hydrophilic nature, allowing the films to be peeled off and removed intact from the glass plates and polyethylene teraphthalate sheets, which could be medically useful considering the majority of transluminal angioplasty balloons are manufactured from polyethylene teraphthalate.

Conclusions

In this example, properties of PLGA films blended with a pore-forming PEG polymer were reported. The effect of PEG molar mass and concentration of the release of paclitaxel, as well as on the mechanical properties of the PLGA films are rationalized on the basis of the nature of the PEG and its distribution within the PLGA. Using confocal Raman mapping, the co-localization of the paclitaxel in the crystalline PEG phase of the phase-separated blends was confirmed. The crystallized PEG is the phase that leaches out first forming the pores for the burst release of associated paclitaxel. Subsequent release of paclitaxel was by diffusion through the dense polymer phase. When the molar mass of PEG was increased, most of the drug was released by burst release, whose extent correlates to the burst release of the crystalline PEG. The phase separation of crystalline PEG in the blend also lowers tensile strength and elongation to break. In general, the lower molar mass PEG allows for greater range of release rate manipulation. Such blended films hold promise for applications requiring enhanced release rates of hydrophobic drugs from hydrophobic matrices.

Example 2

Figure 11:
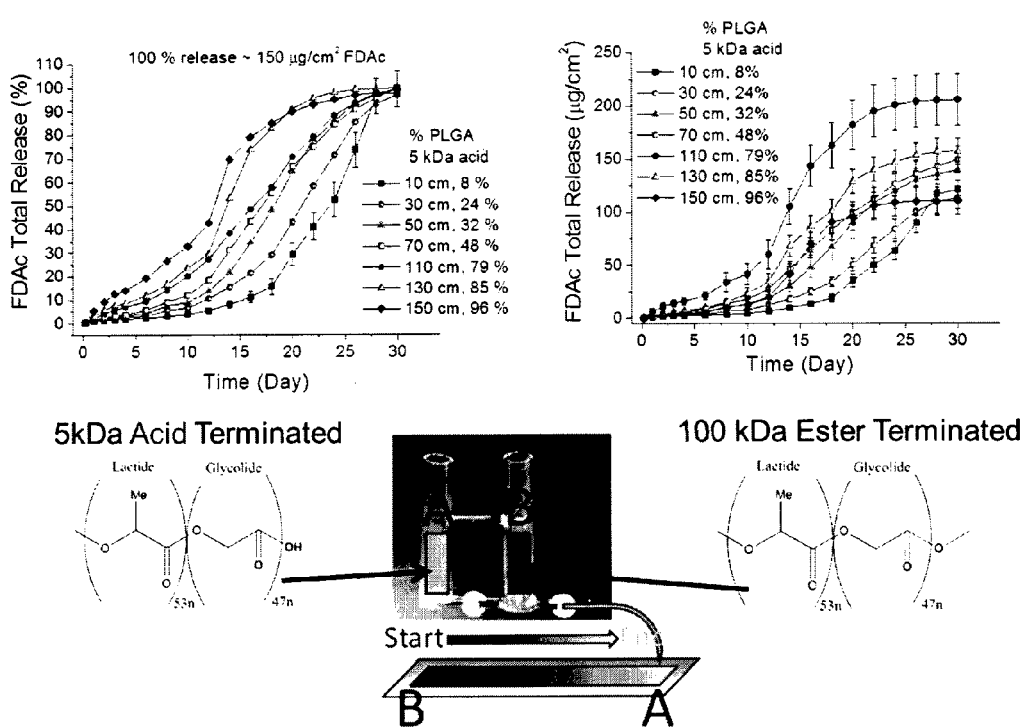
FIG. 11 shows the construction of gradient thin films that allow several controlled drug release profiles through the control of molecular weight distribution and terminal-end group functionality (i.e. the acid terminus of 5 kDa PLGA).

The Effect of PLGA Molecular Weight and Terminal Functional Groups on Drug Release of PLGA Thin Films—Additive-Free PLGA Films with Tuned Drug Delivery Gradient films were produced using the gradient caster shown in FIG. 11. Initially 20 mL of the more viscous solution (15% PLGA (w/v DCM)) was poured into Chamber B, and the additive in Chamber A, i.e. 20 mL 15% PLGA 5 kDa Acid Terminated PLGA (w/v DCM). Each well contained 65 mg (in 20 mL) of fluorescein diacetate (FDAc) for controlled release studies. The gradient maker was tilted at a 10% incline for faster flow rate and fixed to the film applicator with flow rate adjusted by the Teflon stopcock. Chamber B mixing was performed using a battery operated 'Milk Frother' (Ikea, Singapore) modified for overhead mixing and taped into place. Gradient solutions were poured (rate of approximately 20 mL/min) directly into the film applicator within a fume extractor hood. Film applicator height was set at 500 μm and the flowing viscous gradients were directly casted onto 50 μm polyethylene teraphthalate sheets at 20 mm/s, RT, employing a S125 knife caster, capable of 180 cm length films (MTL Systems Pte Ltd, Singapore). DCM was evaporated at RT for 24 h in a fume hood, followed by vacuum oven (<10 Torr) at 55° C. for 48 h. Punch-outs of 5 mm diameter (using a simple paper punch) were taken every 5 or 10 cm for characterization. FIG. 11 displays how varying the terminal functional groups in PLGA can be used to tune the drug release without the use of additives, i.e. PEG.

Figure 12:
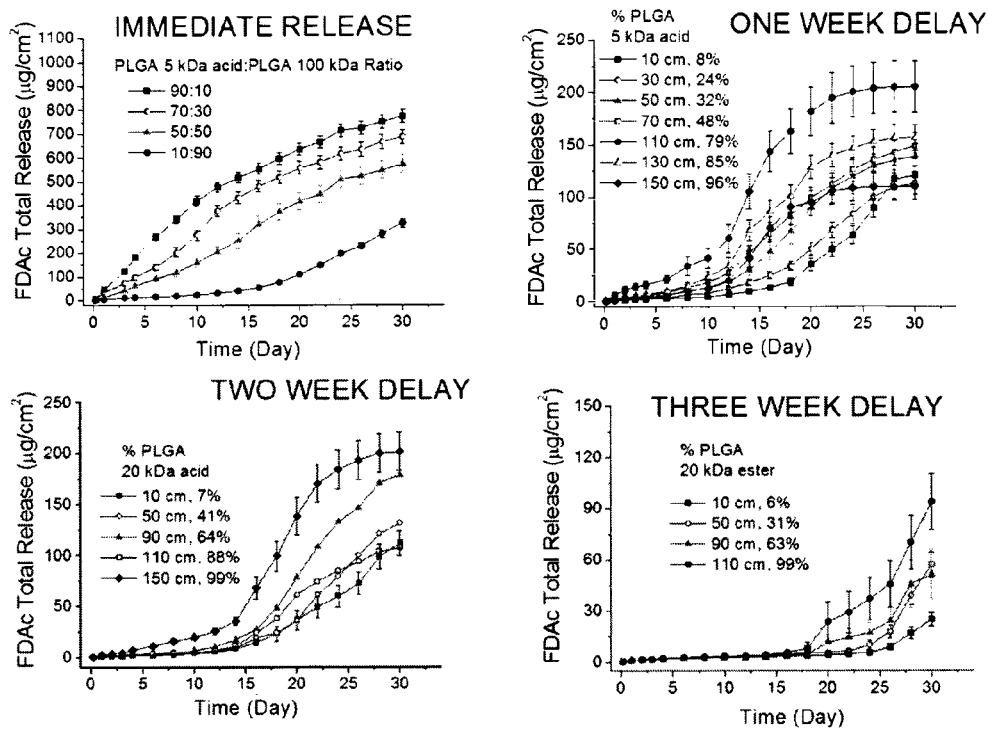
FIG. 12 shows the gradient thin films of PLGA 53/47 100 kDa with ester terminus with additives of PLGA 53/47 5 kDa with acid terminus (2% drug loading), PLGA 53/47 5 kDa with acid terminus (10% drug loading), PLGA 53/47 20 kDa with acid terminus (2% drug loading), or PLGA 53/47 20 kDa with ester terminus (2% drug loading) can deliver drugs with 0-3 weeks of delay if desired.

FIG. 12 displays how the combination of both low molecular PLGA and varying conentrations of carboxyl terminal functional group within the 100 kDa PLGA thin film can be tuned for release rates that have immediate zero order release, one week, two week, and three week delays in drug release.

Figure 13:
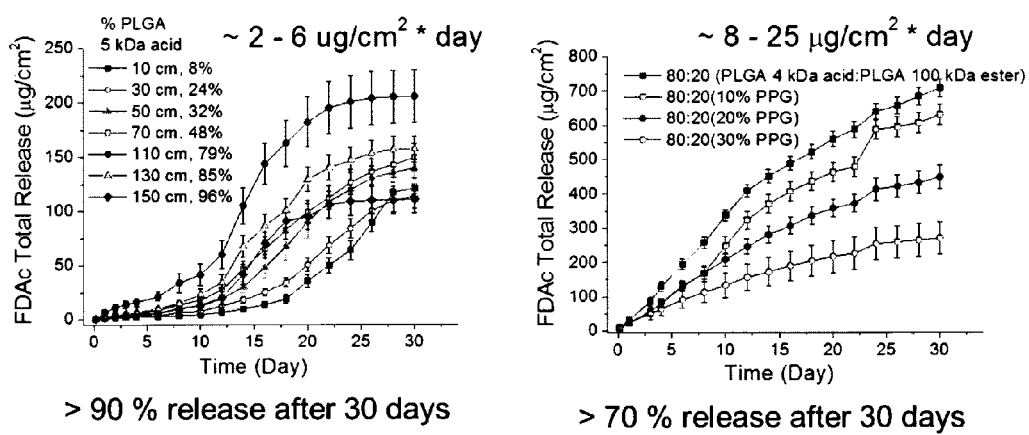
FIG. 13 shows the gradient thin films of PLGA 53/47 100 kDa with ester terminus with additives of PLGA 53/47 5 kDa with acid terminus (2% drug loading), or fixed films of 80:20:0-30% PLGA 53/47 5 kDa with acid terminus: PLGA 53/47 100 kDa with ester terminus: PPG 4 kDA (10% drug loading) can give controlled drug release profiles from 2 to 25 µg/(cm²·day).

FIG. 13 displays how the combinations of polypropylyne glycol, low molecular PLGA, and varying concentrations of carboxyl terminal functional group within the 100 kDa PLGA thin film can be tuned for different rates of controlled drug release, spanning form 2-25 μg cm$^{-2}$ day$^{-1}$ release rates.

Example 3

Figure 14:
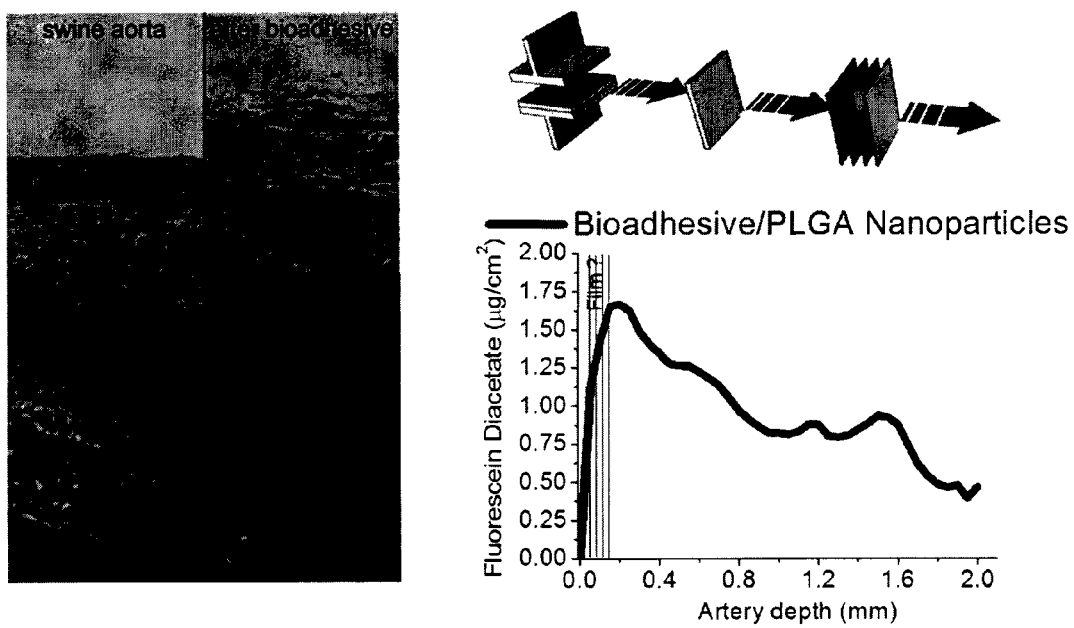
FIG. 14 shows the swine aorta tissue after application of bioadhesive/nanoparticle thin film with fluorescent therapeutic agents. Given the depth of penetration, the therapeutic agents have passed through the tunica intima, tunica media, and into the tunica externa.

The Effect of Bioadhesive Films Containing PLGA/Paclitaxel Nanoparticles on Swine Vascular Tissues Carbopol Bioadhesives (NoAA1-1% w/v, from B.F.G, USA) were blended with PLGA nanoparticles containing 10% fluorescent pro-drug FDAc (fluoroscein diacetate). Bioadhesive/nanoparticle films cast to 30-50 micron thicknesses were tested for tissue adhesion by applying 5N of force and compressed against aorta tissue for 1 min within PBS medium (Phosphate buffer saline, pH 7.4). The detachment force of the films was measured i.e., the force required to peel from the PET sheet. Film transfer observations were noted for transfer completeness hydration characteristics. The fixed aorta tissues from the bioadhesive experiments above were taken and made into 6 mm$^2$ discs, where it was sliced at 50 microns thickness using cryostat sectioner to quantify the fluorescent pro-drug. The slices were treated with 200 μl of RIPA buffer and incubated for 4 hours @ 37° C. to dissolve the tissue and release the drug. The scheme of the overall procedure is given in FIG. 14. After application of the bioadhesive thin films, the swine aortas were fixed and histologically characterized, as seen in FIG. 14. The bioadhesive was able to infiltrate intima and media adventia vascular layers, causing a slight expansion. The infiltrations allows penetration of drug-loaded nanoparticles, where drug can be trapped and released most effectively.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A device for controlled release of a bioactive agent, the device comprising a thin film located on the surface of the device, wherein said thin film comprises a bioactive agent-containing layer comprising a polymeric matrix and at least one bioactive agent, wherein the thin film further comprises a release layer between the bioactive agent-containing layer and the device surface, and wherein the thin film further comprises an adhesive layer on top of the bioactive agent-containing layer, wherein the bioactive agent-containing layer lies between the adhesive layer and the device surface, wherein the adhesion force between the adhesive layer and target tissue is larger than the adhesion force between the release layer and the device surface to allow delaminating of the thin film from the device surface and adhering of the thin film to the target tissue.

2. The device of claim 1, wherein the polymeric matrix of the bioactive agent-containing layer comprises a polymer selected from the group consisting of polyethylene glycol (PEG), PEG fatty acid esters, poly-L-lactic acid (PLLA), poly(lactide-co-glycolide) (PLGA), poly caprolactone (PCL), polyvinyl pyrrolidone (PVP), polyvinyl alcohol (PVA), collagen, chitosan, hydroxy propyl cellulose, polyamides, polyglycerol esters of fatty acids, and combinations thereof.

3. The device of claim 2, wherein the polymeric matrix comprises PLGA and PEG.

4. The device of claim 2, wherein the polymeric matrix comprises between 0 and 50% by weight PEG with the balance being PLGA.

5. The device of claim 2, wherein the polymeric matrix comprises PEG fatty acid esters.

6. The device of claim 5, further comprising one or more fatty acids or fatty alcohols.

7. The device of claim 5, wherein the polymeric matrix comprises 50 to 99% by weight 400 Da PEG distearate and 1 to 50% cetyl alcohol.

8. The device of claim 1, wherein the at least one bioactive agent is encapsulated in a particle.

9. The device of claim 8, wherein the bioactive agent-containing layer comprises 1-50% by weight of the bioactive-encapsulating particles.

10. The device of claim 1, wherein the particle comprises a biodegradable material is selected from the group consisting of polyesters, poly-anhydrides, poly-amides, poly-ketals, poly-acetals, poly-acrylates, lipids, chitosan and gelatin.

11. The device of claim 10, wherein the polyesters are selected from PEG, PLLA, PGLA, PVA, PVP, PCL and combinations thereof.

12. The device of claim 8, wherein the particles have a core-shell structure.

13. The device of claim 12, wherein the at least one bioactive agent is encapsulated in the core of the particle.

14. The device of claim 1, wherein the at least one bioactive agent is selected from pharmaceutical agents, therapeutic agents, diagnostic agents, immunological agents, sensitizing agents, and prophylactic agents.

15. The device of claim 1, wherein the release layer is composed of a polyester wax.

16. The device of claim 1, wherein the adhesive layer is a bioadhesive layer composed of polyacrylic acid (PAA), chitosan, gelatin, collagen, PVA, hydroxyl propyl cellulose, or PVP.

17. The device of claim 15, wherein the polyester wax comprises a PEG fatty acid ester.

18. The device of claim 1, wherein the release layer has a melting temperature of between 35 and 40° C.

19. The device of claim 1, wherein the device is an implant, a surgical instrument or a catheter.

* * * * *